US008865909B2

(12) United States Patent
Srebnik et al.

(10) Patent No.: US 8,865,909 B2
(45) Date of Patent: Oct. 21, 2014

(54) ANTI-BIOFILM AGENTS

(75) Inventors: Morris Srebnik, Mevasseret Zion (IL);
Itzhack Polacheck, Jerusalem (IL);
Doron Steinberg, Jerusalem (IL); Adel Jabbour, Nazareth Ilit (IL); Edward Sionov, Azur (IL)

(73) Assignees: Yissum Research Development Company of the Hebrew University of Jerusalem Ltd., Jerusalem (IL); Hadasit Medical Research Services and Development Ltd., Jerusalem (IL)

( * ) Notice: Subject to any disclaimer, the term of this patent is extended or adjusted under 35 U.S.C. 154(b) by 65 days.

(21) Appl. No.: 13/130,089

(22) PCT Filed: Nov. 19, 2009

(86) PCT No.: PCT/IL2009/001095
§ 371 (c)(1),
(2), (4) Date: Aug. 4, 2011

(87) PCT Pub. No.: WO2010/058402
PCT Pub. Date: May 27, 2010

(65) Prior Publication Data
US 2011/0281921 A1 Nov. 17, 2011

Related U.S. Application Data

(60) Provisional application No. 61/116,480, filed on Nov. 20, 2008.

(51) Int. Cl.
*C07D 277/34* (2006.01)
*A01N 43/76* (2006.01)
*C08G 65/334* (2006.01)
*C07D 207/448* (2006.01)
*A01N 43/50* (2006.01)
*C08F 228/06* (2006.01)
*A01N 37/32* (2006.01)
*C08F 222/40* (2006.01)
*C08G 65/333* (2006.01)
*A01N 43/78* (2006.01)
*C08F 220/14* (2006.01)
*C08F 220/56* (2006.01)

(52) U.S. Cl.
CPC .............. *C07D 277/34* (2013.01); *A01N 43/76* (2013.01); *C08G 65/3348* (2013.01); *C07D 207/448* (2013.01); *C08F 220/14* (2013.01); *A01N 43/50* (2013.01); *C08F 228/06* (2013.01); *A01N 37/32* (2013.01); *C08F 222/40* (2013.01); *C08G 65/33337* (2013.01); *C08F 220/56* (2013.01); *A01N 43/78* (2013.01)
USPC ......................................... 548/183; 514/369

(58) Field of Classification Search
CPC .................................................... C07D 277/34
USPC .............................................. 548/183; 514/369
See application file for complete search history.

(56) References Cited

U.S. PATENT DOCUMENTS

| 2,713,579 | A | 7/1955 | Knott |
| 5,389,658 | A * | 2/1995 | Takatani et al. ............... 514/373 |
| 2001/0021708 | A1* | 9/2001 | Wehner et al. ................. 514/183 |

FOREIGN PATENT DOCUMENTS

| EP | 0143461 | 6/1985 |
| EP | 0522606 | 1/1993 |
| WO | WO 95/35296 | 12/1995 |
| WO | WO 2004/093803 | 11/2004 |
| WO | WO 2008/003085 | 1/2008 |
| WO | WO 2010/058402 | 5/2010 |

OTHER PUBLICATIONS

Kuninobu et al. (Chemistry Letters (2008), 37(7), 740-741).*
Lamiri et al. (CAPLUS Abstract of: Synthetic Communications (2006), 36(11), 1575-1584).*
Mukai et al. (CAPLUS Abstract of: JP02-124878 (1990)).*
International Preliminary Report on Patentability Dated Jun. 3, 2011 From the International Bureau of WIPO Re. Application No. PCT/IL2009/001095.
International Search Report and the Written Opinion Dated Mar. 19, 2010 From the International Searching Authority Re.: Application No. PCT/IL2009/001095.
Ansari et al. "Reaction of Methyl Trans-2,3-Epoxyhexadecanoate With Urea: Synthesis of Long Chain Fatty 2-Oxazolidones", Journal of the American Oil Chemistry Society, JAOCS, XP002572271, 62(12): 1659-1662, 1985. Schemes 1,3: Compound (III).
Ansari et al. Synthesis of Fatty 2-Thiazolines From Fatty Methyl 2,3-Epoxy Ester, Indian Journal of Chemistry, Section B: Organic and Medicinal Chemistry, XP009130434, 26B(2): 146-149, Feb. 1987. Compound (VII).
Brown et al. "Rhodanine Derivatives", Journal of the American Chemical Society, XP002426478, 73: 2357-2359, May 1951. Entry 20 in Table 1.
Freiberg et al. "Novel Bacterial Acetyl Coenzyme A Carboxylase Inhibitors with Antibiotic Efficacy In Vivo", Antimicrobial Agents and Chemotherapy, 50: 2707-2712, 2006.
Ginak et al. "Synthesis of 5-Alkyl(benzyl)idene-3-Hydroxymethyl-2-Thioxothiazolidin-4-Ones" Russian Journal of General Chemistry, 73: 1663-1664, 2003.
Heerding et al. "New Benzylidenethiazolidinediones as Antibacterial Agents", Bioorganic and Medicinal Chemistry Letters, 13: 3771-3773, 2003.
Hogan "Talking to Themselves: Autoregulation and Quorum Sensing in Fungi", Eukaryotic Cell, 5: 613-619, 2006.

(Continued)

*Primary Examiner* — Robert Havlin

(57) ABSTRACT

Novel agents exhibiting anti-biofilm formation activity while being non-cytotoxic are provided, as well as methods of using the same, either per se or conjugated to a polymer, for preventing and/or reducing the formation of microbial biofilms and/or for disrupting microbial biofilms. The novel agents described herein include thiazolidine-2,4-diones (TZDs), pyrrolidine-2,5-diones (PYDs), imidazolidine-2,4-diones or oxazolidine-2,4-diones, substituted by an alkyl having 7-20 carbon atoms in its backbone chain.

21 Claims, 11 Drawing Sheets
(10 of 11 Drawing Sheet(s) Filed in Color)

(56) References Cited

OTHER PUBLICATIONS

Hogan et al. "A *Pseudomonas aeruginosa* Quorum-Sensing Molecule Influences *Candida albicans* Morphology", Molecular Microbiology, 54: 1212-1223, 2004.
Huang et al. "A Novel Three-Component Reaction of Allenoates, Isocyanides, and Carboxylic Acids: Facile Synthesis of Highly Substituted Acryl Imide Derivatives", Journal of Organic Chemistry, XP002572274, 73: 1173-1175, Oct. 1, 2008. Product 11f in Table 3.
Jung et al. "Facile Preparation of Alkylidenesuccinimides From Maleimides via the Phosphoniosilylation Process", Bulletin of the Korean Chemistry Society, XP002572269, 25(7): 1088-1090, 2004. Compounds 5e, 5j.
Kaplan "Methods for the Treatment and Prevention of Bacterial Biofilms", Expert Opinion on Therapeutic Patents, XP002383461, 15(8): 955-965, Jan. 1, 2005.
Kawato et al. "Novel Peptidomimetics of the Antifungal Cyclic Peptide Rhodopeptin: Synthesis of Mimetics and Their Antifungal Activity", Organic Letters, XP002300247, 3(22): 3451-3454, Jan. 1, 2001. Compound 6.
Lesyk et al. "4-Thiazolidones: Centenarian History, Current Status and Perspectives for Modern Organic and Medicinal Chemistry", Current Organic Chemistry, 8: 1547-1577, 2004.
Mangaleswaran et al. "An Easy Access to (E)-Alkylidenesuccinic Acids", Synthesis, XP002572273, 3: 343-345, 2003. Compounds 4c-4e.
Meanwell et al. "Diethyl 2,4-Dioxoimidazolidine-5-Phosphonates: Horner—Wadsworth—Emmons Reagents for the Mild and Efficient Preparation of C—5 Unsaturated Hydantoin Derivatives", Journal of Organic Chemistry, XP002572272, 56: 6897-6904, 1991. Entry 3 in Table IV (Product 26c).
Mizufune et al. "Process Research on Arylnaphthalene Lignan Aza-Analogues: A New Palladium-Catalyzed Benzannulation of $\alpha,\beta$ Bisbenzylidenesuccinic Acid Derivatives", Tetrahedron, 62: 8539-8549, 2006.
Ohishi et al. "Preparations of 5-Alkylmethylidene-3-Carboxymethylrodanine Derivatives and Their Aldose Reductase Inhibitory Activity", Chemical and Pharmaceutical Bulletin, XP009130428, 38(7): 1911-1919, Jul. 1990. Compound 3f in Chart I, Table 1 and on p. 1917.
Ozinskas et al. "Synthesis of L-Canaline and γ-Functional 2-Aminobutyric Acid Derivatives", The Journal of Organic Chemistry, 51: 5047-5050, 1986.
Pohlmann et al. "Pyrrolidinedione Derivatives as Antibacterial Agents with a Novel Mode of Action", Bioorganic and Medicinal Chemistry Letters, 15: 1189-1192, 2005.
Russell et al. "Selective Small Molecule Inhibitors of the Potential Breast Cancer Marker, Human Arylamine N-Acetyltransferase 1, and Its Murine Homologue, Mouse Arylamine N-Acetyltransferase 2", Bioorganic & Medicinal Chemistry, XP025893465, 17(2): 905-918, Jan. 15, 2009. Scheme 2, Compounds 61-63 in Table 5 and on p. 917.
Wagenaar et al. "Intramolecular Nucleophilic Catalysis by the Neighboring Hydroxyl Group in Acid-Catalyzed Benzenesulfonamide Hydrolysis", The Jpurnal of Organic Chemistry, 49: 3445-3448, 1984.
Yale "Synthetic Hypoglycemic Agents. I", Journal of the American Chemistry Society, XP002572270, 75: 675-678, 1953. Table on p. 678: Entries 4, 8.
Communication Pursuant to Article 94(3) EPC Dated May 7, 2013 From the European Patent Office Re. Application No. 09796470.4.

\* cited by examiner

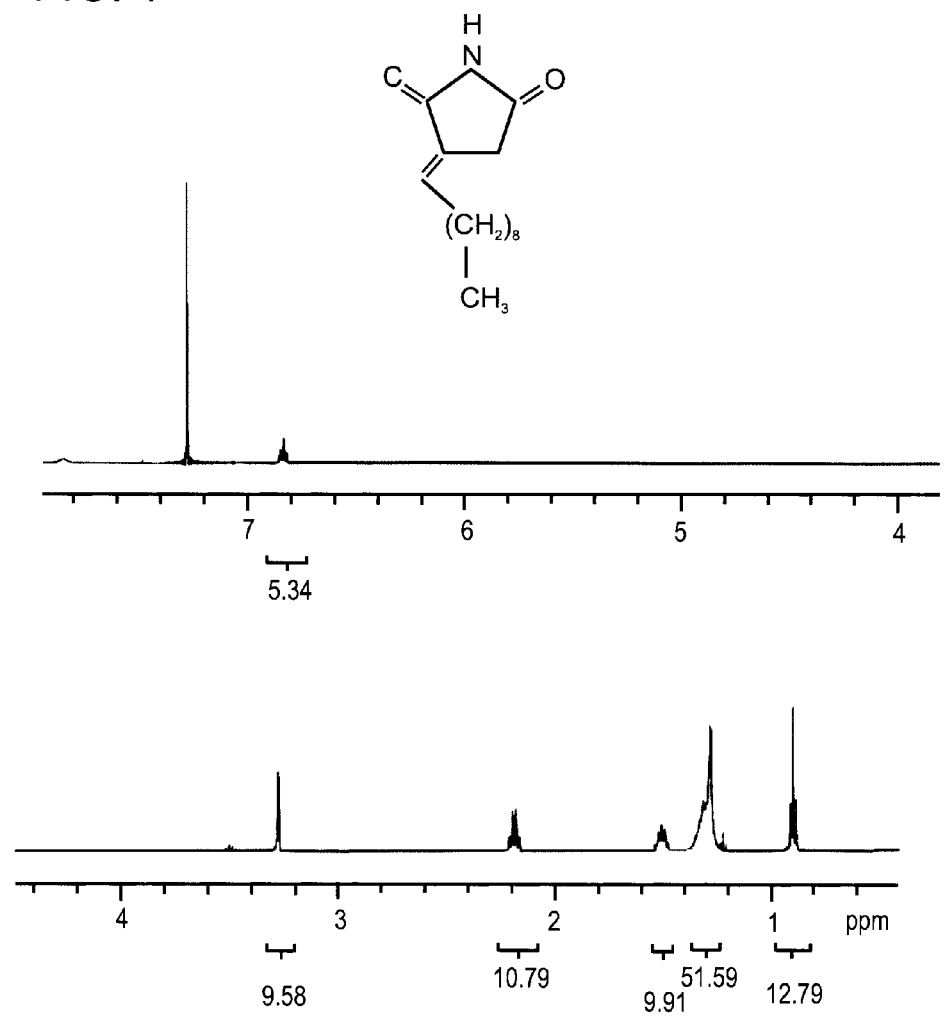

ANTI-BIOFILM AGENTS

RELATED APPLICATIONS

This application is a National Phase of PCT Patent Application No. PCT/IL2009/001095 having International filing date of Nov. 19, 2009, which claims the benefit of priority of U.S. Provisional Patent Application No. 61/116,480 filed on Nov. 20, 2008. The contents of the above applications are all incorporated herein by reference.

FIELD AND BACKGROUND OF THE INVENTION

The present invention, in some embodiments thereof, relates to novel anti-microbial agents and more particularly, but not exclusively, to novel agents that are capable of preventing biofilm formation and/or reducing biofilm mass, and to uses thereof in various applications.

Many bacteria are planktonic, namely they move freely around in water and other liquid media, however, many pathogenic and harmful microorganisms are or become sessile, namely attached to a surface where they form biofilms. Biofilms are a multicellular high density ecological environment of mostly bacteria and/or fungi and their secretions, but it is not considered a multicellular organism per se. Once a microorganism attach to a surface it undergoes a series of changes, the most obvious of which is the excretion of a slimy material consisting mostly of extra-cellular polysaccharides (EPS). EPS, soluble microbiological products (SMP), dispersed bacterial cells, and a well characterized natural organic matter (NOM) have all been identified as part of a "conditioning layer" that may help retain other fouling materials, as well as directly cause membrane biofouling.

A dramatic phenotypic change occurs as the bacteria turn or switch from a planktonic to a biofilm state and attach to a surface; a whole different suite of genes is activated, making sessile bacteria significantly different to planktonic bacteria suspended in the water. Biofilm bacteria have been found to remain viable at MICs (minimal inhibitory concentration) up to 1,000 times higher than those of their planktonic counterparts. Biofilms have been shown to alter the local environment to enhance their survival, changing such properties as pH and the dissolved oxygen concentration. These changes can reduce the effectiveness of some treatments. For example, biofilms are known to vary the local pH, and some oral biofilms have regions of pH less than 4.9.

In addition to their complex, heterogeneous composition, biofilms are also dynamic hydrogels which capriciously move, detach and reform on a wide variety of environmental or engineered surfaces. Thus, when water-borne bacteria congregate in sufficient numbers they may form a film on the surface of pipes, tanks, and indeed any piece of equipment, and biofouling usually results. Biofouling can be defined as the unspecific adsorption of biological material onto surfaces upon their immersion in a fluid. EPS secreted by bacteria and other colonizing microorganisms envelope and anchor them to the substrate thereby altering the local surface chemistry which can stimulate further growth such as the recruitment and settlement of microorganisms. Biofouling via biofilm formation causes the deterioration in the microbiological quality of water by inducing biocorrosion termed microbiologically influenced corrosion and biofouling of piping, membranes, containers and reservoirs.

Biofilms also interrupt the flow of ions and water to and from the substrate surface by acting as a diffusion barrier. The reduction of localized oxygen by cathodic reactions within the electrolyte can accelerate the corrosion of a metallic substrate by creating a differential aeration concentration cell. The corrosion and weathering caused by biofilm can lead to considerable damage to heat exchangers, unexpected corrosion of stainless steel, and premature destruction of membranes, and many other technological, industrial and homestead aliments.

Both bacteria and fungi share the same habitat in the oral cavity, although they belong to different kingdoms in the evolution hierarchy. They both harbor mixed biofilms which cover oral tissues. *Streptococcus mutans* is a cardinal member of the oral biofilm associated with dental caries while *Candida albicans* is associated with oral candidiasis. Bacteria can communicate therebetween by what is known as quorum sensing (QS) which is effected by secreting small molecules termed auto inducers (AI's) into their environment. This phenomenon affects many physiological and metabolic pathways of bacteria, including the formation of biofilms and antibacterial resistance. Recently, eukaryotic cells such as fungi have also been shown to communicate with each other by producing AIs, however, the AIs of bacteria and fungi differ chemically. Quorum sensing takes place especially in biofilms were the microbes are at close proximity to one another.

Inter species QS may affect microbes' physiology and virulence properties resulting in enhanced virulent properties of biofilms. Small peptides, AI-2 (furanosyl borate diester), AI-1 (N-acylhomoserine lactones) and C-AI (Cholera AI) have been shown to act as signal molecules in QS in many types of bacteria, including oral bacteria.

The study of bacterial QS has suggested several ideal targets for manipulation of QS, mainly the AI-2 signal molecule or its sensor-2, due to the wide distribution of the AI-2 cascade in many types of bacteria.

Similarly, it has been reported recently that also fungi communicate between themselves with signal molecules, and production of farnesol by *C. albicans* at high cell densities is the first QS system which has been discovered in eukaryotes. Farnesol has been identified as QS agent that blocks the morphological transition from yeast to the filament form and affects biofilm formation in *C. albicans*. The mechanism by which farnesol is sensed by *C. albicans* is not yet known. Farnesoic acid and tyrosol were also shown to posses AI properties in *C. albicans*.

Eukaryotes seem to have evolved efficient mechanisms to manipulate bacterial QS and thereby protect themselves from pathogenic bacterial attack and competition [Hogan, D. A., 2006, *Eukaryot Cell*, 5, 613-9]. Thus, by producing quorum sensing inhibitors (QSIs), the eukaryotic host may be simultaneously conversing with a variety of different bacterial strains that it encounters in its natural habitat, potentially encouraging the beneficial ones and antagonizing the harmful strains. Parallel to this, certain bacteria have evolved mechanisms to fine-tune gene regulation of eukaryotic with their QS signals [Hogan D. A. et al., 2004, *Mol. Microbiol.*, 54, 1212-23]. This eukaryote-bacterial cross talk could be exploited to model manipulative techniques that interfere with bacterial QS.

Hence, it has been established that bacteria and fungi immobilized in the form of biofilms are inherently more robust and resistant to antibiotics and antifungal agents than the planktonic forms. Those mixed biofilms constitute a basis of numerous infections and diseases and are responsible in part to the growing emergence of resistance to antimicrobial agents. Thus, small compounds that can interfere with QS can offer a new approach to the development of novel antimicrobial and anti-biofilm agents. It is now evident that influencing QS in microbes harboring biofilms bears great potential as a novel non-antimicrobial, alternative means of affecting pathogenic microbes.

Cell harvesting and tissue dissociation is widely used in science and medicine. Harvesting single cells, for study, analyses, identification, pathology, processing or subculture propagation, either of unicellular or multicellular organisms, oftentimes requires dissociation or detachment of single cells from a biofilm or a tissue.

While cell harvesting is a routine procedure in handling and propagating tissue culture cell lines, tissue disaggregation is used for the establishment of primary cultures, and for the release of cell from a whole tissue for medical treatments. Primary cultures are a widely used tool in molecular biology, toxicology, and biotechnology. An example of cells release for medical use is the isolation of fibroblasts from skin biopsy for future skin transplantations. The tissue dispersion into a cell suspension is usually achieved by a combined mechanical and enzymatic procedure. The enzyme should be able to degrade the extra-cellular matrix components, such as collagen. The enzymatic procedure is frequently performed in combination with ion chelator such as EDTA.

The most commonly used enzyme for tissue disaggregation and cell harvesting is porcine- or bovine-derived trypsin. It was formerly thought that trypsin preparations simply hydrolyzed a proteinaceous adhesive bonding substance responsible for the tenacious attachment of cells to their substratum with the resultant detachment of the cells from the culture vessel. It is now assumed that the mechanism of action of trypsin in cell harvesting is more complex. Trypsin is most frequently used since it is effective for many tissues, and demonstrated to be well tolerated by many cell types, however, the exposure of cells to active enzymes should be minimized to preserve maximum viability, and hence trypsin inhibitors are used in most procedures.

Other methods for cells harvesting and tissue dissociation involve the use of plant or bacterial enzymes, such as *Clostridium histolyticum* collagenases, plant cardosins, and the commercial microbially-produced product GIBCO™ Protease™.

The presence of a thiazolidine ring in penicillins and related derivatives was the first recognition of its occurrence in nature, and since then many thiazolidine derivatives have shown antifungal or antibacterial activity [Heerding D. A. et al., 2003, *Bioorg Med Chem Lett.*, 13, 3771-3].

The chemistry of thiazolidinediones (TZDs) has been extensively reviewed [Lesyk R. B. and Zimenkovsky B. S., 2004, Current Organic Chemistry, 8, 1547-77]. Furthermore, the interest in 2,4-thiazolidinedione derivatives has been heightened markedly during the last years due to their potential use as a new class of antidiabetic (insulin-sensitizing) agents (troglitazone, pioglitazone and darglitazone), that are currently used for the treatment of type-II Diabetes Mellitus.

(Z)-3-(octan-2-ylidene)-5-thioxopyrrolidin-2-one and (Z)-1-(hydroxymethyl)-3-(octan-2-ylidene)-5-thioxopyrrolidin-2-one, two thioxo derivatives of the short-alkyl TZDs (Z)-3-(octan-2-ylidene)pyrrolidine-2,5-dione and (Z)-1-(hydroxymethyl)-3-(octan-2-ylidene)-5-thioxopyrrolidin-2-on, respectively, have been reported by Ginak, A. I. et al. [Russian Journal of General Chemistry (Translation of Zhurnal Obshchei Khimii), 73(10), 1663-1664; 2003].

Pyrrolidinediones have been investigated for antibacterial activity and have shown a unique mechanism of action. The chemistry and activity of pyrrole-2,5-diones (PYDs) has been reviewed by, for example, Pohlmann, J. et al., *Bioorganic and Medicinal Chem. Let.*, 15 (2005), pp. 1189-1192; Freiberg, et al., *Antimicrobial Agents And Chemotherapy*, 2006, pp. 2707-2712; Ozinskas A. J. et al., *J. Org. Chem.*, 1986, 51, 26, pp. 5047-5050; and Mizufune, H. et al., Tetrahedron, 62 (2006), pp. 8539-8549.

WO 95/35296 discloses condensed imidazole compounds, their production and use as adhesion molecule expression inhibitors, and in passing mentions the intermediate compound (Z)-3-butylidenepyrrolidine-2,5-dione as a reactant or a reagent, which is a short-alkyl PYD derivative.

Barrett, Anthony G. M. et al. [J. Org. Chem., 1984, 49, 19, pp 3673-4 and J. Org. Chem., 1986, 51, 4, pp 495-503] report the synthesis of showdomycin and epi-showdomycin by cyclization of (E)-3-(2,3,4,5-tetrahydroxypentylidene)pyrrolidine-2,5-dione, and in passing mentions (E)-3-(4 hydroxybutylidene)pyrrolidine-2,5-dione, (Z)-3-(5-hydroxyhexylidene)pyrrolidine-2,5-dione and (E)-3-(4-hydroxypentylidene)pyrrolidine-2,5-dione, all of which are short-alkyl PYD derivatives.

SUMMARY OF THE INVENTION

The present inventors have recognized the structural elements required of molecules to inhibit both bacterial and fungal quorum sensing (QS) simultaneously, and conceived a family of novel compounds, some of which are based on a thiazolidinedione (TZD) skeleton, some based on pyrrole-2,5-dione (PYD) skeleton, some based on 5-substituted-pyrimidine-2,4-dione (PMD) skeleton and some are based on 5-substituted-2-thioxo-2,3-dihydropyrimidin-4(1H)-one (TPMD) skeleton, all of which are characterized by a long-chain substituent branching off the main ring. These molecules were shown to inhibit QS in several microorganisms, such as *Vibrio harveyi* and *Candida albicans*, and as a result, these agents can substantially prevent or significantly retard biofilm formation of colonizing microorganisms. Accordingly, these agents can be used effectively in various therapeutic applications as well as in maintaining clean water sources, piping, filters, membranes, containers and reservoirs in households, desalinations plants, drinking fountains, closed-loop cooling towers, air conditioning ducts and related applications. These agents can further be incorporated into polymers for use in the long-term prevention of biofilm induced biofouling of surfaces of objects such as medical devices, as well as pipes and membranes involved in water treatment, water purification and for use in drinking water. For short-term use, i.e., cleansing and washing large surfaces, these agents can be formulated as a rinsing composition.

Hence, according to embodiments of one aspect of the present, there is provided a compound having the general formula:

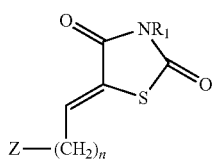

Formula A1 or a salt thereof,
wherein:
n is an integer ranging from 7 to 20;
Z is selected from the group consisting of H, —CH$_3$, —C(=O)Q, a linking moiety, a reactive group, a polymer moiety and a polymerizable moiety;
Q is selected from the group consisting of —OH, —OR$_3$, —NR$_4$R$_5$ and —NHOH;

R₁ is selected from the group consisting of H, alkyl and —(CH₂)ₘCO₂R₇;

M is an integer ranging from 1 to 6; and

R₃, R₄, R₅ and R₇ are each independently selected from the group consisting of H, alkyl and aryl.

According to some embodiments of the invention, R₁ is H.

According to some embodiments of the invention, the compound according to Formula A1 is selected from the group consisting of (Z)-5-decylidenethiazolidine-2,4-dione (TZD10); (Z)-5-octylidenethiazolidine-2,4-dione (TZD8); (Z)-5-undecylidenethiazolidine-2,4-dione (TZD11); (Z)-5-dodecylidenethiazolidine-2,4-dione (TZD12); (Z)-5-hexadecylidenethiazolidine-2,4-dione (TZD16); and (Z)-5-octadecylidenethiazolidine-2,4-dione (TZD18).

According to some embodiments of the invention, R₁ is the —(CH₂)ₘCO₂R₇.

According to some embodiments of the invention, the compound according to Formula A1 is selected from the group consisting of (Z)-methyl 2-(5-decylidene-2,4-dioxothiazolidin-3-yl)acetate (TZD10MA); (Z)-ethyl 2-(5-decylidene-2,4-dioxothiazolidin-3-yl)acetate (TZD10EA); (Z)-2-(5-decylidene-2,4-dioxothiazolidin-3-yl)acetic acid (TZD10AA); and sodium (Z)-2-(5-decylidene-2,4-dioxothiazolidin-3-yl)acetate (TZD10AANa).

According to embodiments of another aspect of the present, there is provided a compound having the general formula:

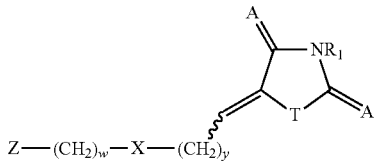

Formula I or a salt thereof,
wherein:
y and w are each independently an integer, such that y+w ranges from 7 to 20;

A is selected from the group consisting of O, S and NR₁₀;

T is selected from the group consisting of —S—, —O—, —CH₂— and —NR₆—;

R₁ is selected from the group consisting of H, alkyl, aryl, heteroaryl, alicyclic, heterocyclic and —(CH₂)ₘCO₂R₇;

m is an integer ranging from 1 to 6;

X is selected from the group consisting of —CH₂—, —CR₈R₉—, —O—, —S— and —NR₂— or absent;

Z is selected from the group consisting of H, —CH₃, —C(=O)Q, a linking moiety, a reactive group, a polymer moiety and a polymerizable moiety;

Q is selected from the group consisting of —OH, —OR₃, —NR₄R₅ and —NHOH; and

R₂, R₃, R₄, R₅, R₆, R₇, R₈, R₉ and R₁₀ are each independently selected from the group consisting of H, alkyl, aryl, heteroaryl, alicyclic and heterocycli According to some embodiments of the invention, A is O.

According to some embodiments of the invention, T is —S—.

According to some embodiments of the invention, R₁ is H.

According to some embodiments of the invention, X is absent.

According to some embodiments of the invention, A is O, T is —S—, R₁ is H, y+w is 8 and Z is —CH₃.

According to some embodiments of the invention, X is O.

According to some embodiments of the invention, R₁ is H or the —(CH₂)ₘCO₂R₇.

According to some embodiments of the invention, the compound according to Formula I is selected from the group consisting of (Z)-5-decylidenethiazolidine-2,4-dione (TZD10); (Z)-5-octylidenethiazolidine-2,4-dione (TZD8); (Z)-5-undecylidenethiazolidine-2,4-dione (TZD11); (Z)-5-dodecylidenethiazolidine-2,4-dione (TZD12); (Z)-5-hexadecylidenethiazolidine-2,4-dione (TZD16); (Z)-5-octadecylidenethiazolidine-2,4-dione (TZD18); (Z) 5-(5-(decyloxy)pentylidene)thiazolidine-2,4-dione (TZD1c); (Z)-methyl 2-(5-decylidene-2,4-dioxothiazolidin-3-yl)acetate (TZD10MA); (Z)-ethyl 2-(5-decylidene-2,4-dioxothiazolidin-3-yl)acetate (TZD10EA); (Z)-2-(5-decylidene-2,4-dioxothiazolidin-3-yl)acetic acid (TZD10AA); and sodium (Z)-2-(5-decylidene-2,4-dioxothiazolidin-3-yl)acetate (TZD10AANa).

According to some embodiments of the invention, T is CH₂.

According to some embodiments of the invention, R₁ is H.

According to some embodiments of the invention, X is absent.

According to some embodiments of the invention, Z is —CH₃.

According to some embodiments of the invention, the compound according to Formula I is selected from the group consisting of (E)-3-decylidenepyrrolidine-2,5-dione (PYD10); and (E)-3-octylidenepyrrolidine-2,5-dione (PYD8).

According to some embodiments of the invention, the compounds presented herein are for use in a method of preventing or reducing an anti-biofilm formation and/or disrupting a biofilm.

According to some embodiments of the invention, the compounds presented herein are substantially non-toxic to microorganisms at a concentration lower than 10 mM.

According to some embodiments of the invention, the compounds presented herein further include a polymer moiety or a polymerizable moiety covalently attached thereto.

According to some embodiments of the invention, Z is a linking moiety, and the polymer moiety or polymerizable moiety is attached to the compound via the linking moiety.

According to some embodiments of the invention, the polymer moiety is selected from the group consisting of a polyacrylate, a polymethacrylate, a polyethylene glycol, an oligosaccharide, a peptide, a nucleic acid, a polyurethane, an epoxy resin, a fluoropolymer, a polyimide, a polyamide, a polyacrylamide, polyhydroxyethyl methacrylate and N-vinyl-2-pyrrolidinone.

According to some embodiments of the invention, the compounds presented herein which include a polymer moiety or a polymerizable moiety covalently attached thereto are for use in a method of preventing or reducing a formation of a biofilm on a surface of a substrate.

According to some embodiments of the invention, the method is effected by applying the compound on the surface of the substrate.

According to some embodiments of the invention, the compounds presented herein which include a polymer moiety or a polymerizable moiety covalently attached thereto are substantially non-toxic to microorganisms at a concentration lower than 10 mM.

According to embodiments of another aspect of the present, there is provided a composition which includes, as an active ingredient, a compound as presented herein and a carrier.

According to some embodiments of the invention, the composition is identified for use in a method of preventing or reducing a formation of a biofilm or disrupting a biofilm.

According to some embodiments of the invention, the composition is packaged in a packaging material and identified in print, in or on the packaging material, for use in a method of preventing or reducing a formation of a biofilm or disrupting a biofilm.

According to some embodiments of the invention, the method is effected by treating a medical condition wherein preventing or reducing a formation of a biofilm and/or disrupting a biofilm in a subject is beneficial.

According to some embodiments of the invention, the carrier is a pharmaceutically acceptable carrier.

According to some embodiments of the invention, the composition further including one or more additional active agent.

According to some embodiments of the invention, the additional active agent is an antimicrobial agent.

According to some embodiments of the invention, the composition includes the compounds presented herein which include a polymer moiety or a polymerizable moiety covalently attached thereto; the composition is identified for use in a method of preventing a formation of a biofilm on a surface of a substrate.

According to some embodiments of the invention, the composition is packaged in a packaging material and identified, in or on the packaging material for use in the method of preventing a formation of a biofilm on a surface of a substrate.

According to embodiments of another aspect of the present, there is provided an anti-biofilm composition including the compound presented herein.

According to embodiments of another aspect of the present, there is provided a method of treating a medical condition wherein preventing or reducing a formation of a biofilm and/or disrupting a biofilm in a subject is beneficial, the method is effected by administering to the subject in need thereof a pharmaceutically effective amount of the compound presented herein.

According to some embodiments of the invention, the method of treating further includes administering to the subject an additional active agent.

According to some embodiments of the invention, the additional active agent is an antimicrobial agent.

According to embodiments of another aspect of the present, there is provided a use of the compound presented herein in the manufacture of a medicament for treating a disease or disorder in which reducing or preventing the formation of a biofilm and/or disrupting a biofilm in a subject is beneficial.

According to some embodiments of the invention, the compound is used in combination with an additional active agent.

According to some embodiments of the invention, the additional active agent is an antimicrobial agent.

According to embodiments of another aspect of the present, there is provided a method of reducing a biofilm mass in a substrate, the method is effected by contacting the substrate with an effective amount of the compound presented herein.

According to embodiments of another aspect of the present, there is provided a method of preventing a formation of a biofilm on a substrate, the method is effected by applying to a surface of the substrate an effective amount of the compounds presented herein which include a polymer moiety or a polymerizable moiety covalently attached thereto.

According to embodiments of another aspect of the present, there is provided a method of harvesting living cells from a biofilm, the method is effected by contacting the biofilm with an effective amount of a compound as described herein, to thereby release the cells; and collecting the cells.

As used herein the term "about" refers to ±10%.

The terms "comprises", "comprising", "includes", "including", "having" and their conjugates mean "including but not limited to". The term "consisting of" means "including and limited to".

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The words "optionally" or "alternatively" are used herein to mean "is provided in some embodiments and not provided in other embodiments". Any particular embodiment of the invention may include a plurality of "optional" features unless such features conflict.

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a biomolecule" or "at least one biomolecule" may include a plurality of biomolecules, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

Figure 2A:
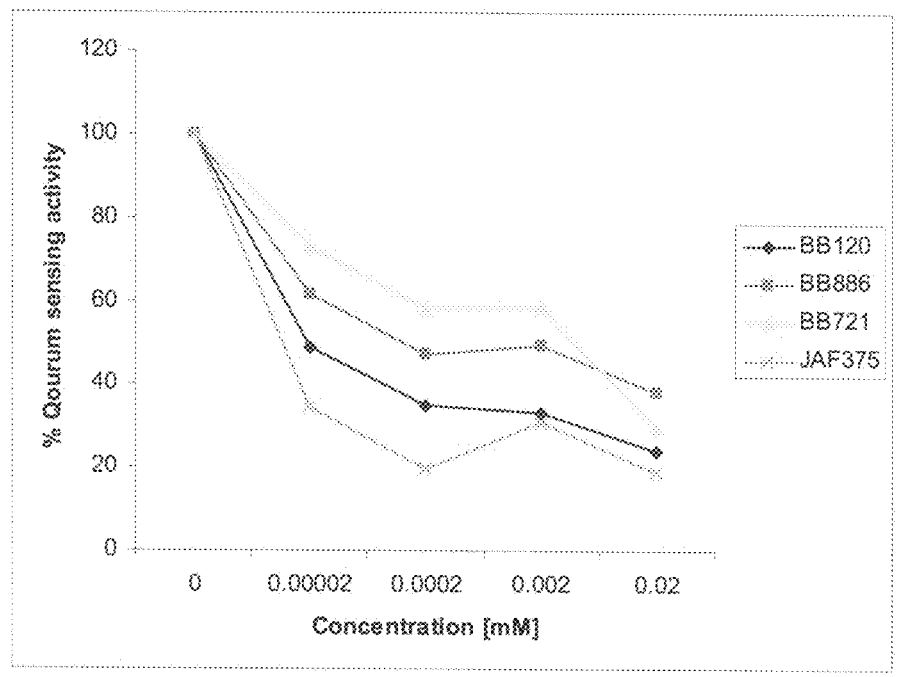
Figure 2B:
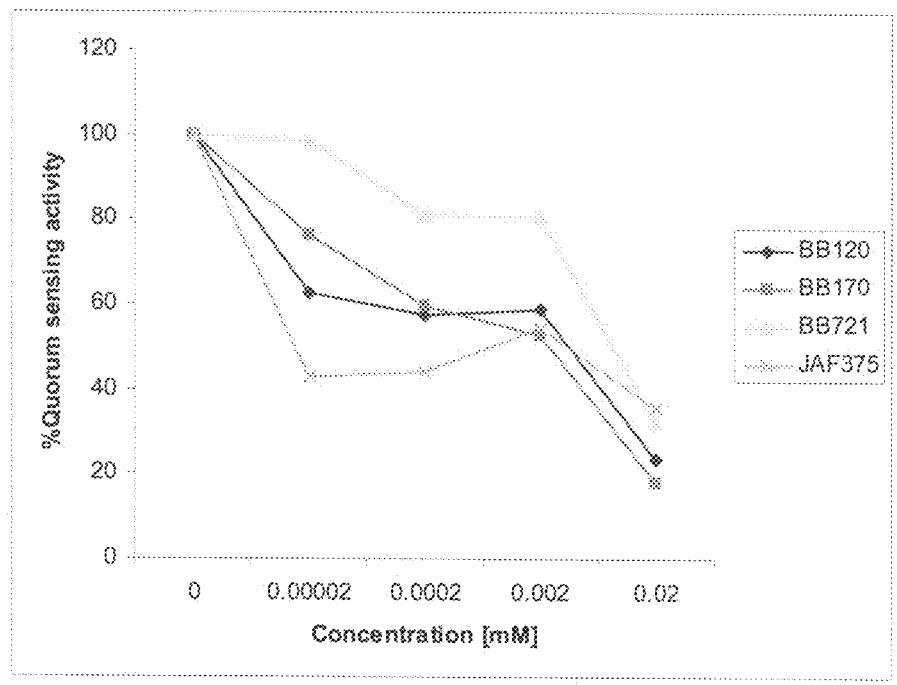
Figure 2C:
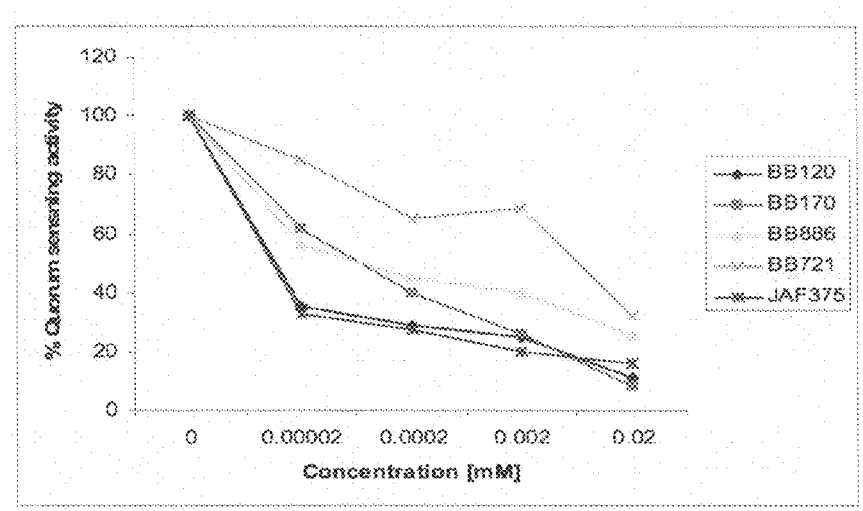
Figure 3A:
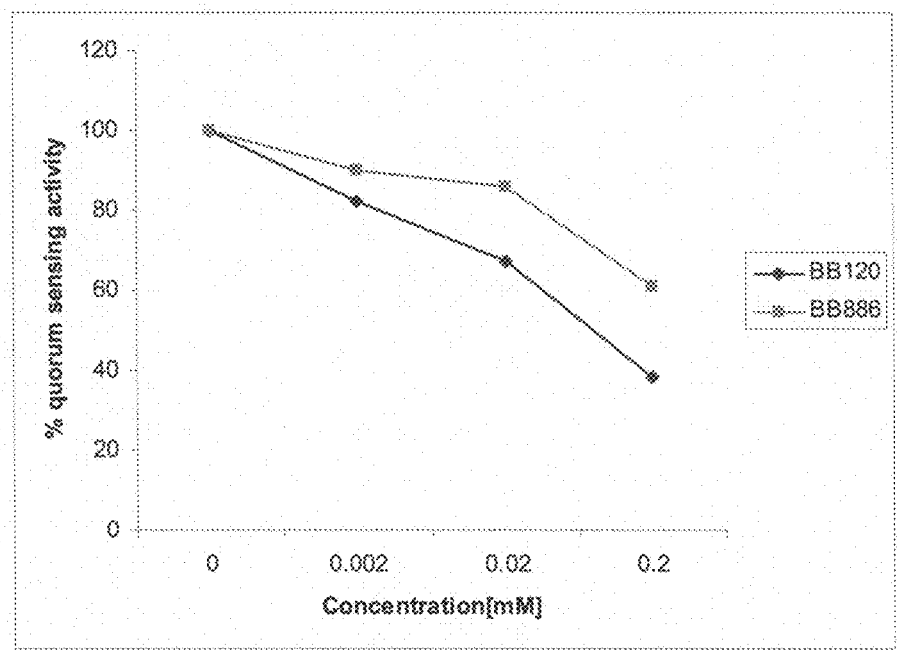
Figure 3B:
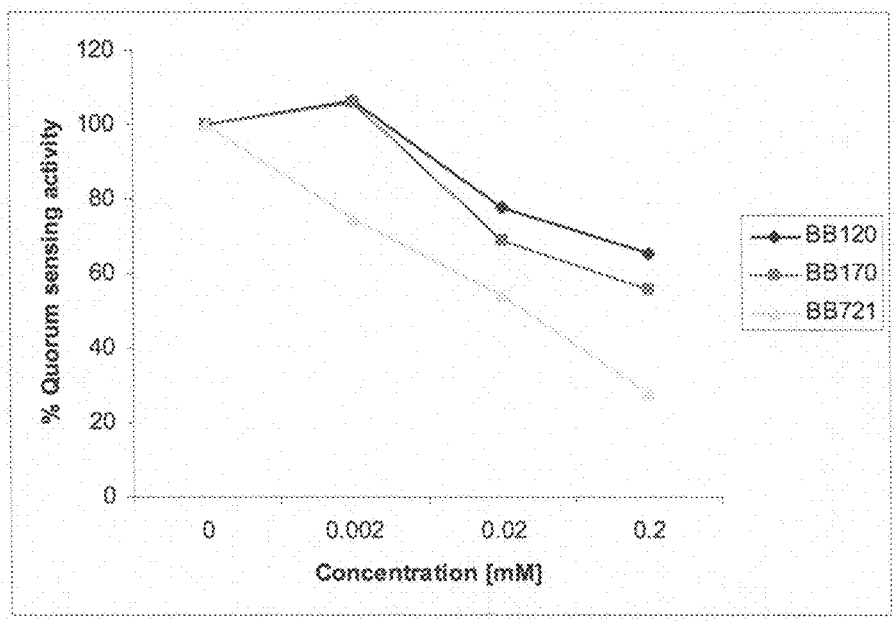
Figure 3C:
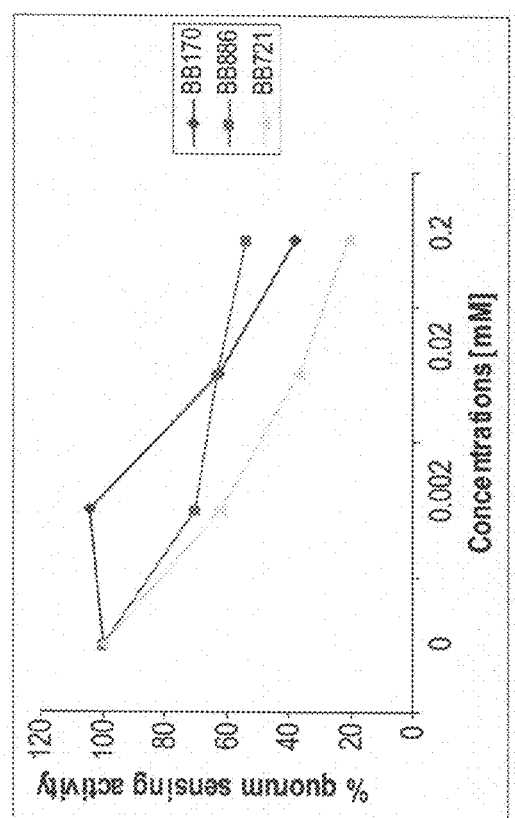
Figures 4A, 4B, 4C, 4D:
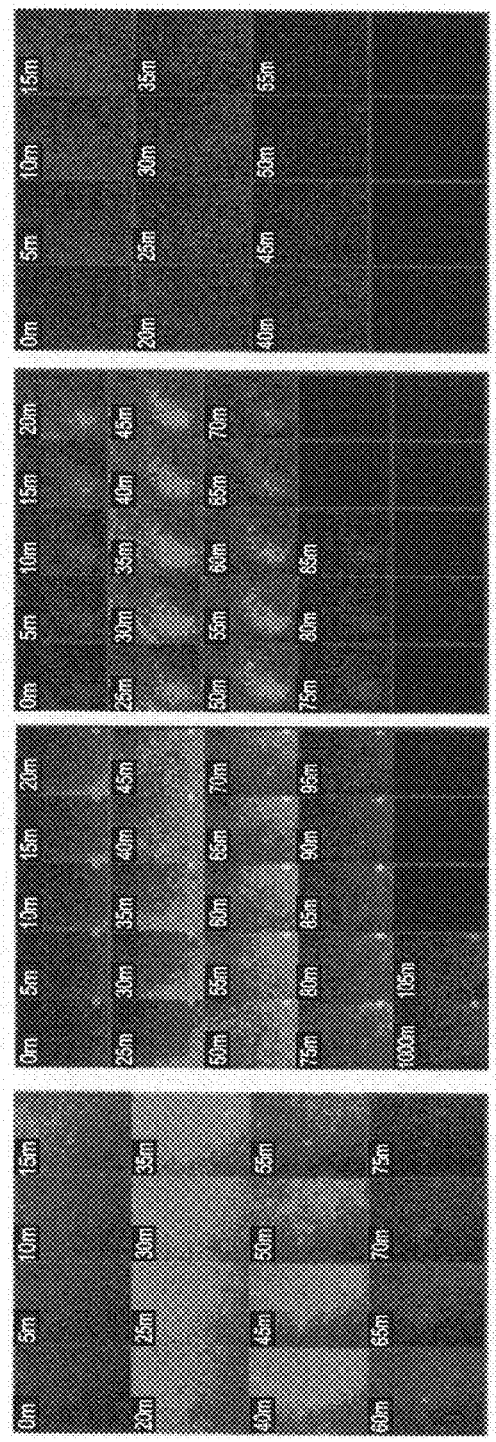
Figure 5:
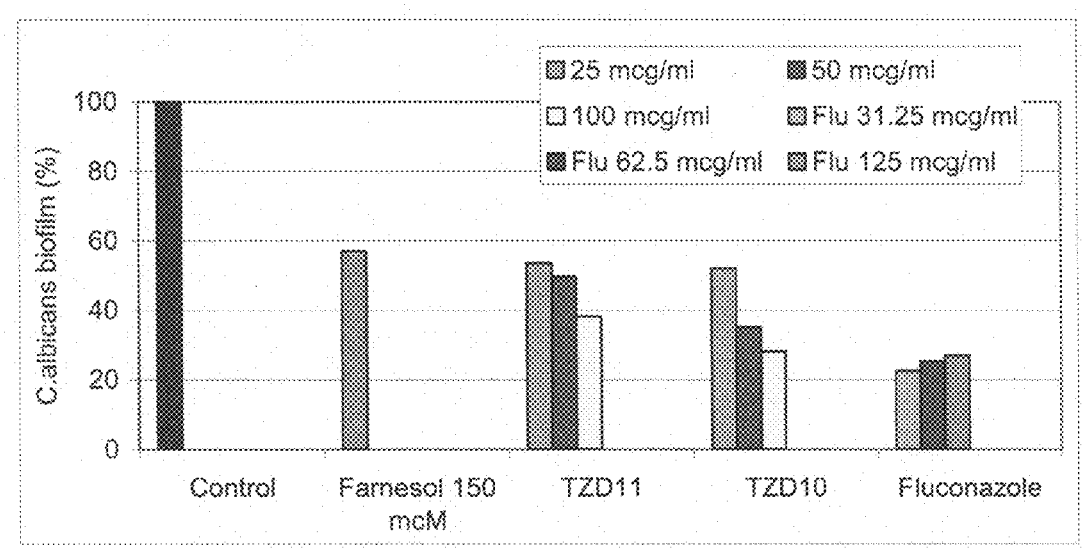
Figure 6:
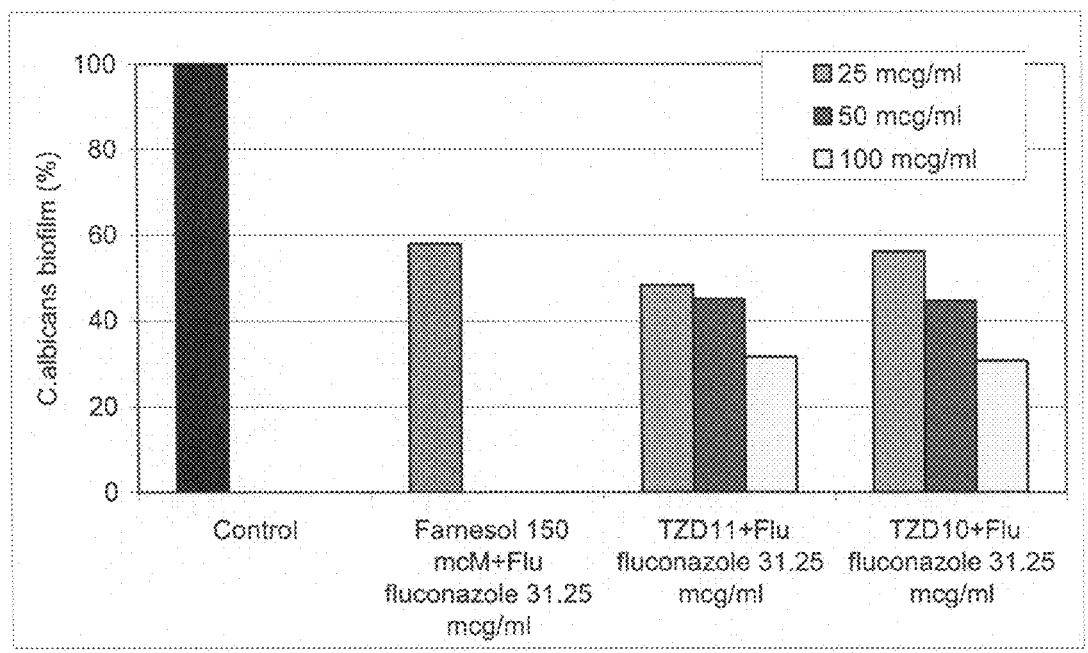
Figure 7:
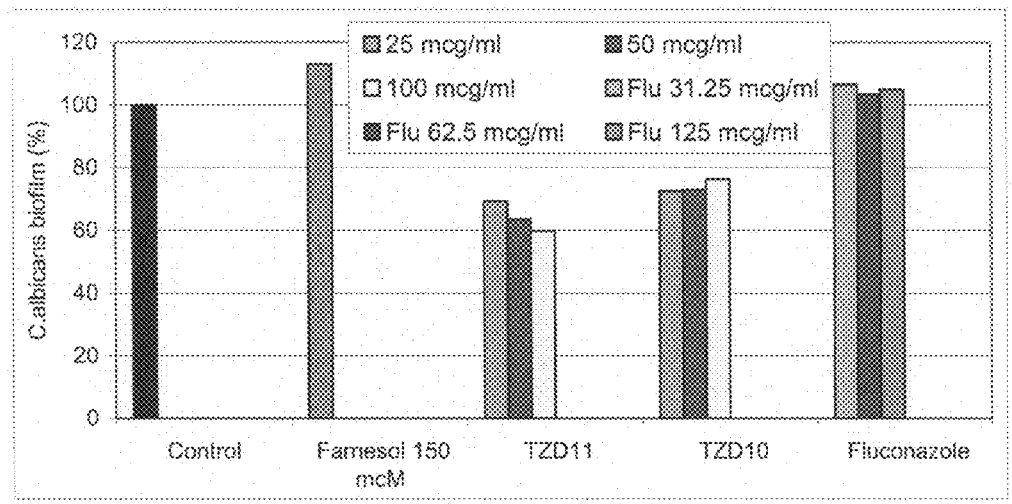
Figure 8:
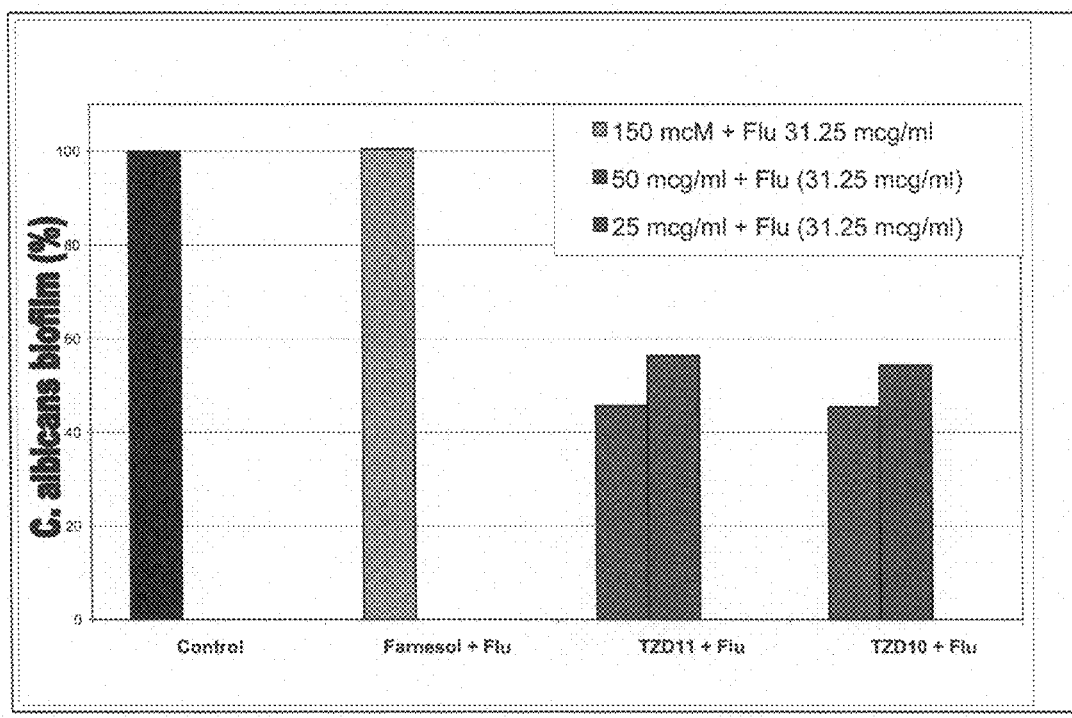
Figure 9:
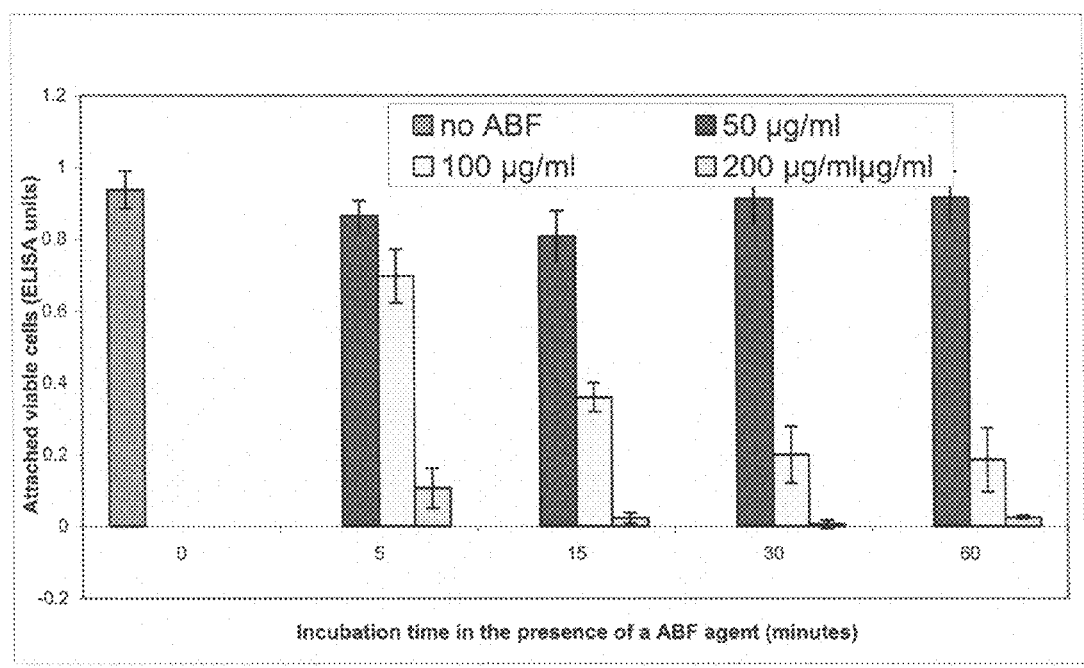
Figure 10:
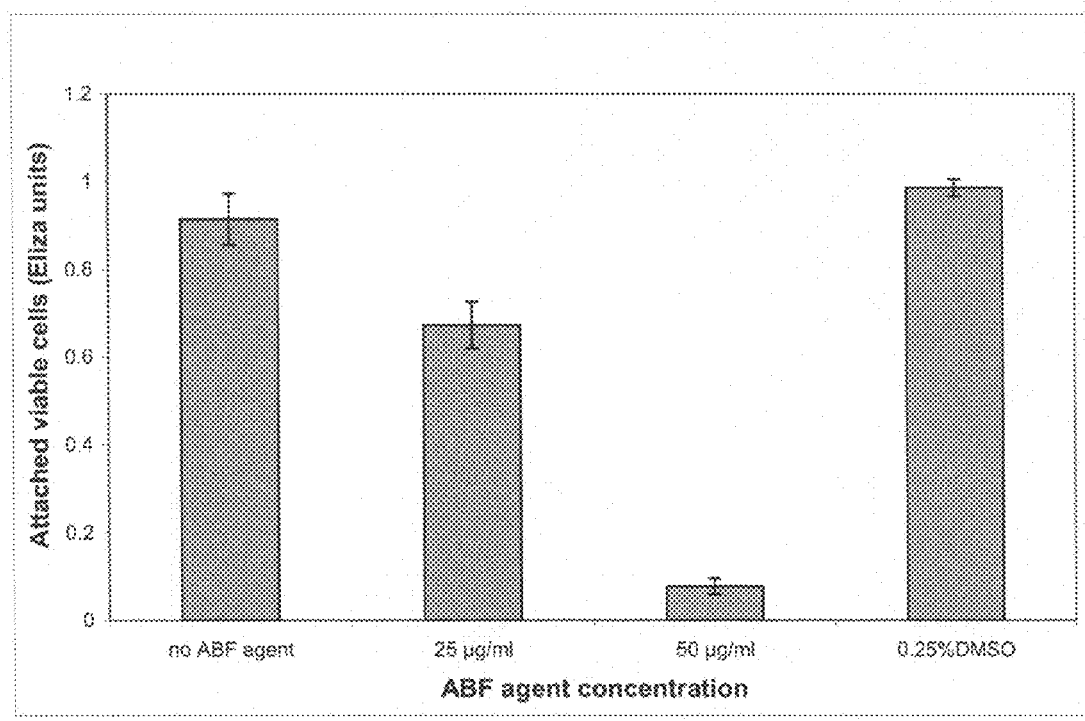
Figure 11:
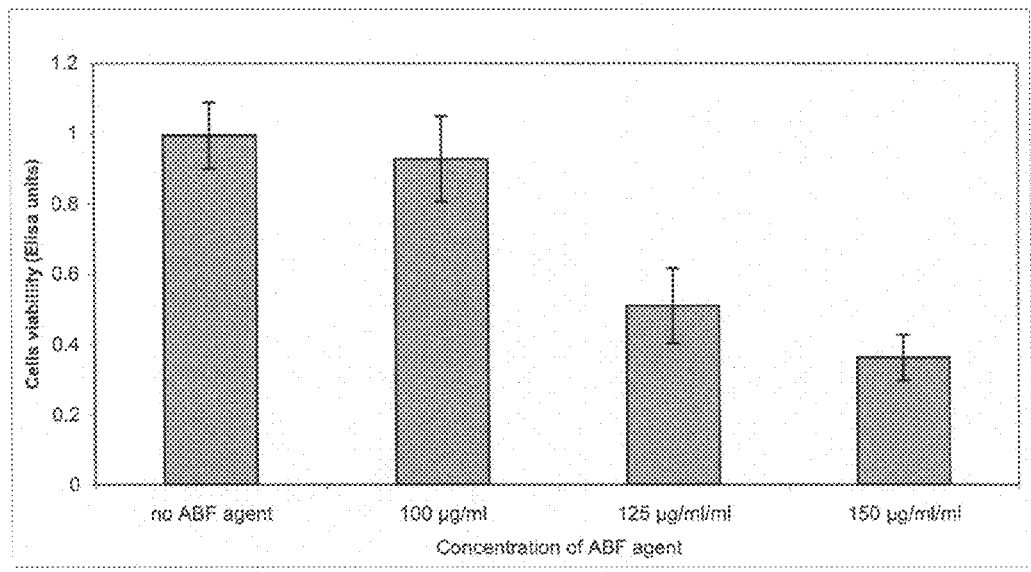
Figure 12:
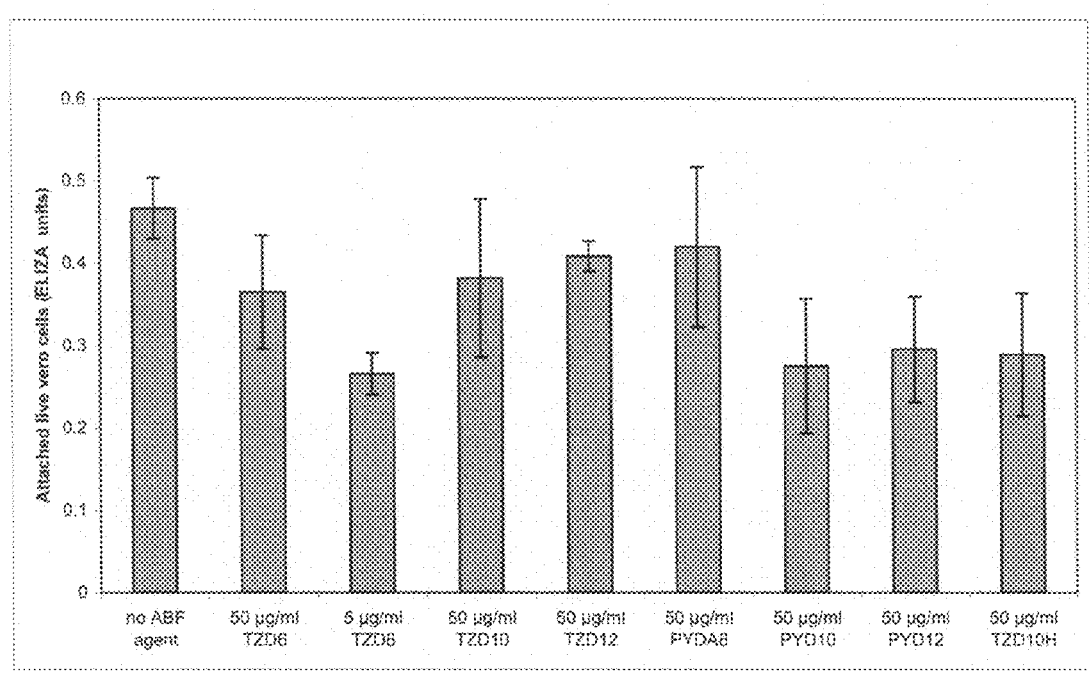
Figure 13A:
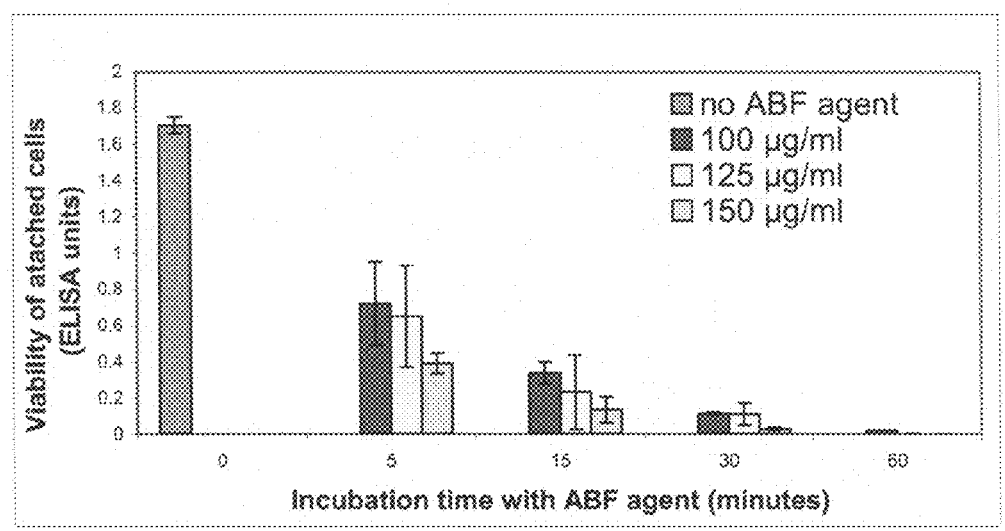
Figure 13B:
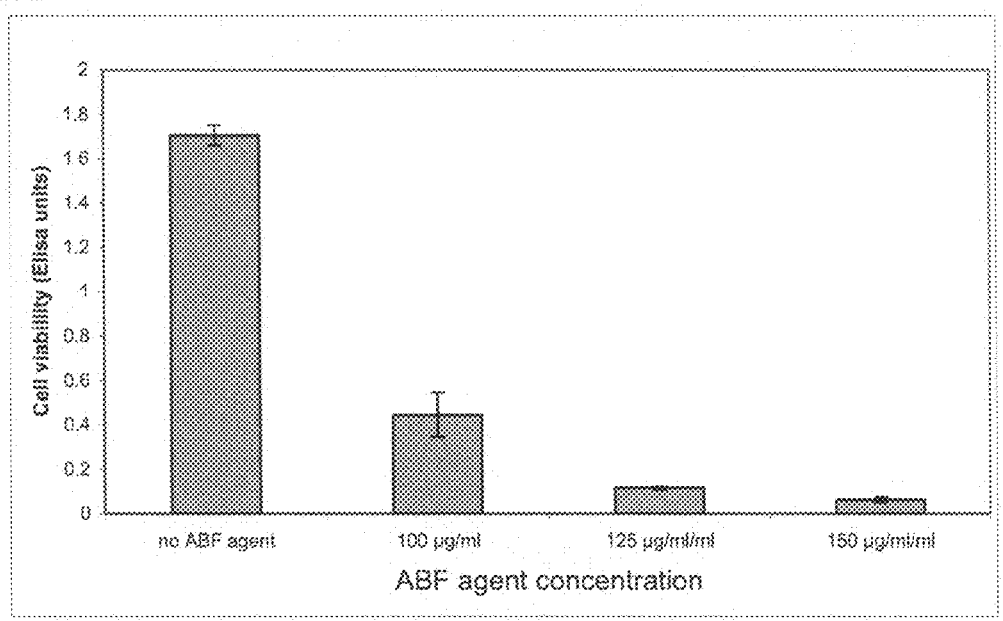

FIG. 1 presents the $^1$H NMR spectra of (E)-3-decylidenepyrrolidine-2,5-dione (PYD10), an exemplary anti-biofilm formation (ABF) agent according to embodiments of the present invention;

FIGS. 2A-C present the effect of TZD10, an exemplary ABF agent according to embodiments of the present invention, on quorum sensing in *V. harveyi* strains BB120 (wild type), BB170 (sensor 1$^-$), BB886 (sensor 2$^-$), BB721 (LuxO null) and JAF375 (sensor 1$^-$ and 2$^-$) in planktonic conditions, by following omitted luminescence as an indicator of quorum sensing, with the addition of 10% v/v spent medium of AI-1 (FIG. 2A), AI2 (FIG. 2B) and AI0 (FIG. 2C), showing a classic dose-response curve and thereby demonstrating the effectiveness of the ABF agent in *V. harveyi* regardless of the presence or absence of AI or quorum sensing genes;

FIGS. 3A-C present the effect of TZD10, an exemplary ABF agent according to embodiments of the present invention, on *V. harveyi* mutants (BB120 (wild type), BB170 (sensor 1$^-$), BB886 (sensor 2$^-$), BB721 (LuxO null), JAF375 (sensor 1$^-$ and 2$^-$) in mature biofilm conditions, by following omitted luminescence as an indicator of quorum sensing, with the addition of 10% (v/v) spent medium of AI-1 (FIG. 3A), AI-2 (FIG. 3B) and AI-0 (FIG. 3C);

FIGS. 4A-D present photographs of luminescent *V. harveyi* cells immobilized in the form of biofilms, showing the biofilm disruption effect of TZD10, an exemplary ABF agent according to embodiments of the present invention, on matured biofilms of *V. harveyi* wild-type strain (BB120) at different concentrations of 0 µM control (FIG. 4A), 2 µM (FIG. 4B), 20 µM (FIG. 4C) and 200 µM (FIG. 4D), wherein the biofilms are visualized by green emission, varying in intensities as a function of the amount of labeled bacteria, corresponding to the depth of the biofilm staring from the surface interface to the air/water interface, and wherein each of the individual frames represent a depth point in microns, going row-wise from 0 micron at the top-left frame to 75 microns at the bottom-right frame;

FIG. 5 presents a comparative bar-graph of the results of the QSI experiments in the fungus *C. albicans* as assessed by colorimetric assay and microscopy, which demonstrated that incubation of *C. albicans* yeast cells (in planktonic form) with farnesol, the exemplary ABF agents TZD10 and TZD11, according to embodiments of the present invention, and anti-fungal agent fluconazole, showing that the present ABF agents inhibited germination and substantially prevented biofilm formation;

FIG. 6 presents a comparative bar-graph of the results of the QSI experiments in the fungus *C. albicans* as presented in FIG. 5, whereas in this experiments the ABF agents were removed after 48 hours and fluconazole 31.25 µg/ml was introduced for another 24 hours;

FIG. 7 presents comparative bar-graph of the synergistic effect of farnesol and one of the exemplary ABF agents TZD10 and TZD11, on mature biofilm of *C. albicans* as presented in FIG. 5 without the presence of fluconazole;

FIG. 8 presents comparative bar-graph of the synergistic effect of farnesol and one of the exemplary ABF agents TZD10 and TZD11, on mature biofilm of *C. albicans* as presented in FIG. 5 with the presence of fluconazole;

FIG. 9 presents a comparative bar-graph showing the results of the Vero cells detachment assay using TZD10, an exemplary ABF agent according to the present invention, demonstrating the effectiveness of TZD10 to detach living cells from the cell-aggregate;

FIG. 10 presents a bar-graph showing the results of the Vero cells detachment assay after overnight incubation with 50 µg/ml of TZD10, an exemplary ABF agent according to the present invention, demonstrating that most of the cells are still viable;

FIG. 11 presents the results of the Vero cell viability assay, wherein the cell viability was measured after 160 minutes incubation with TZD10, an exemplary ABF agent according to some embodiments of the present invention;

FIG. 12 presents a bar-graph showing the results obtained for a series of ABF agents, according to some embodiments of the present invention, which were tested as suitable for Vero cell harvesting; and FIGS. 13A-B present bar-graphs showing the results of the assay for detachment of MDCK cells by TZD10, an exemplary ABF agent according to some embodiments of the present invention (FIG. 13A), and the MDCK cells viability assay after incubation with TZD10 (FIG. 13B).

DESCRIPTION OF EMBODIMENTS OF THE INVENTION

The present invention, in some embodiments thereof, relates to novel anti-microbial agents and more particularly, but not exclusively, to novel agents that are capable of preventing biofilm formation and/or reducing biofilm mass, and to uses thereof in various applications.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, biofilm of bacteria, fungi, algae and other microorganisms present a formidable challenge in the battle against biofouling, particularly in internal medicinal and dentistry fields, as well as in fields such as water treatment, containment and transportation.

The present inventors have studied compounds of the thiazolidine family, and serendipitously found that some derivatives of thiazolidine exert quorum sensing inhibitory activity, and hence can be used as anti-biofilm agents.

The present inventors have uncovered that in order to exhibit anti-biofilm activity, but not necessarily anti-microbial activity, the thiazolidine derivative should include a long-chain substituent.

The present inventors have further uncovered that these novel compounds can be used both as anti-biofilm disinfecting compositions, as active ingredients in anti-microbial pharmaceutical compositions, and can also be tethered to monomers or polymers to the end of using these agents to coat surfaces which must be kept free of biofilm, thereby protecting these surfaces for extended and even unlimited period of time.

Hence, some embodiments of the present invention concern new chemical entities which can exert anti-biofilm formation (ABF) activity and methods of their syntheses, as well as uses of these compounds in a variety of applications wherein the formation of biofilm is highly undesirable or hazardous.

Thus, according to an aspect of some embodiments of the present invention, there are provided novel compounds, which are referred to herein also as anti-biofilm formation (ABF) compounds or agents. In some embodiments, the novel compounds disclosed herein can be collectively represented by the general formula I:

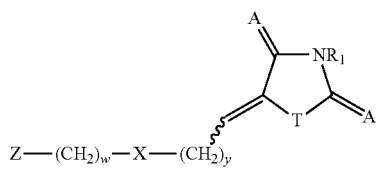

Formula I wherein:

A is selected from the group consisting of O, S and $NR_{10}$;

T is selected from the group consisting of —S—, —O—, —$CH_2$— and —$NR_6$—;

each of y and w are integers, whereas y+w ranges from 7 to 20;

$R_1$ is selected from the group consisting of H, alkyl, aryl, heteroaryl, alicyclic, heterocyclic and —$(CH_2)_mCO_2R_7$;

m is an integer ranging from 1 to 6;

X is selected from the group consisting of —$CH_2$—, —$CR_8R_9$—, —O—, —S— and —$NR_2$— or absent;

Z is selected from the group consisting of H, —$CH_3$, —C(=O)Q, a linking moiety, a reactive group, a polymer moiety and a polymerizable moiety, as defined herein;

Q is selected from the group consisting of —OH, —$OR_3$, —$NR_4R_5$ and —NHOH; and $R_2$, $R_3$, $R_4$, $R_5$, $R_6$, $R_7$, $R_8$, $R_9$ and $R_{10}$ are each independently selected from the group consisting of H, alkyl, aryl, heteroaryl, alicyclic and heterocycli In some embodiments, other novel ABF compounds as described herein can be collectively represented by general Formula II:

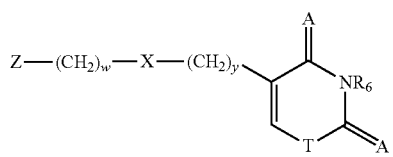

Formula II wherein the variables in Formula II are as follows:

A is selected from the group consisting of O, S and $NR_{10}$;

Z is selected from the group consisting of H, —$CH_3$, —C(=O)Q, a linking moiety, a reactive group, a polymer moiety and a polymerizable moiety, as defined herein;

X is selected from the group consisting of —$CH_2$—, —$CR_8R_9$—, —O—, —S— and —$NR_2$— or absent;

y and w are integers, whereas y+w ranges from 7 to 20;

Q is selected from the group consisting of —OH, —$OR_3$, —$NR_4R_5$ and —NHOH;

T is selected from the group consisting of —S—, —O—, —$CH_2$—, —$NR_6$— and —$NR_7$—; and $R_{10}$, $R_2$, $R_3$, $R_4$, $R_5$, $R_6$ and $R_7$ are each independently selected from the group consisting of H, alkyl, aryl, heteroaryl, alicyclic (cycloalkyl) and heteroalicyclic (heterocyclic).

The present embodiments further encompass any enantiomers, prodrugs, solvates, hydrates, salts and/or pharmaceutically acceptable salts of the compounds described herein, either as specific embodiments or under a general formula.

The compounds presented herein can exhibit several isomeric, enantiomeric or otherwise configurationally different structures, as all are encompassed under the general formulae presented herein. For example, in Formula I the substituent at the fifth position on the TZD ring can have a cis or trans configuration, or in more absolute terms it can have the Z or E configuration, where in some case one of the isomers can exhibit activity attributes which are exhibited in the opposite isomer to a lesser extent. According to some embodiments of the present invention, the configuration of the ABF agents belonging to the TZD family take the Z-configuration, and the ABF agents belonging to the PYD family take the E-configuration. However, other configurations are also contemplated.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester, or amine group which is administered as an amide (the "prodrug"). Such a prodrug is hydrolyzed in vivo, to thereby provide the free compound (the parent drug). The selected ester may affect both the solubility characteristics and the hydrolysis rate of the prodrug. Prodrugs, according to some embodiments of the present invention, can be made using succinic acid, maleic acids, fumaric acids and the likes.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. An example, without limitation, of a pharmaceutically acceptable salt would be a carboxylate anion and a cation such as, but not limited to, ammonium, alkylammonium, sodium, potassium and the like.

The novel compounds described herein are generally nitrogen-containing, dioxo (or dithiooxo or diimine) 5-membered or 6-membered heterocyclic compounds, which comprise an alkylene substituent that is attached to an unsaturated moiety within the core structure.

The core of the compounds presented herein is a heterocyclic ring, having at least one chain substituent which is denoted Z—(CH2)$_w$—X—(CH$_2$)$_y$, wherein w and y are integers which partially signify the length of the chain. According to embodiments of the present invention, the chain is a long alkyl chain, which may be interrupted by one of more heteroatoms in cases where X is —O—, —S— or —NR$_2$—, and may terminate with a non-methyl group in cases where Z is —C(=O)Q, an amine, a linking moiety, a reactive group, a polymer moiety or a polymerizable moiety, as these terms are defined hereinbelow.

As used herein, the term "alkyl" describes an aliphatic hydrocarbon including straight chain and branched chain groups. Preferably, the alkyl group has 1 to 20 carbon atoms, and more preferably 1-10 carbon atoms. Whenever a numerical range; e.g., "1-10", is stated herein, it implies that the group, in this case the alkyl group, may contain 1 carbon atom, 2 carbon atoms, 3 carbon atoms, et, up to and including 10 carbon atoms. In the context of the resent invention, a "long alkyl" is an alkyl having at least 7 carbon atoms in its main chain (the longest path of continuous covalently attached atoms). A short alkyl therefore has 6 or less main-chain carbons. The alkyl can be substituted or unsubstituted. When substituted, the substituent can be, for example, an alkyl, an alkenyl, an alkynyl, a cycloalkyl, an aryl, a heteroaryl, a halide, an amine, a hydroxyl, a thiol, an alkoxy and a thioalkoxy, as these terms are defined herein.

The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, hydroxy, alkoxy and thioalkoxy. Representative examples are piperidine, piperazine, tetrahydrofurane, tetrahydropyrane, morpholino and the like.

The term "hydroxy", as used herein, refers to an —OH group.

The term "alkoxy" refers to a —OR' group, were R' is alkyl, aryl, heteroalicyclic or heteroaryl.

As used herein, the term "amine" describes a —NR'R" group where each of R' and R" is independently hydrogen, alkyl, cycloalkyl, heteroalicyclic, aryl or heteroaryl, as these terms are defined herein.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted by one or more substituents, as described hereinabove.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

As used herein, the terms "halo" and "halide", which are referred to herein interchangeably, describe an atom of a halogen, that is fluorine, chlorine, bromine or iodine, also referred to herein as fluoride, chloride, bromide and iodide.

The term "haloalkyl" describes an alkyl group as defined above, further substituted by one or more halide(s).

The term "alkoxy" refers to a —OR' group, were R' is as defined herein.

The term "thiohydroxyl" or "thiol", as used herein, refers to an —SH group.

The term "thioalkoxy" refers to a —SR' group, were R' is as defined herein.

In some embodiments, T in Formula I is S, and A is O, such that the compounds belong to the family of thiazolidinediones (TZDs).

In some embodiments, T in Formula I is S, and A is S, such that the compounds belong to the family of thiazolidinedithiones.

In some embodiments, T in Formula is CH$_2$ and A is O, such that the compounds belong to the family of pyrrole-2,5-diones (PYDs).

In some embodiments, T in Formula is CH$_2$ and A is S, such that the compounds belong to the family of pyrrole-2,5-dithiones.

According to some embodiments, X is absent, such that the substituent is an alkyl. In some of these embodiments, the value of y+w is at least 6, and in some embodiments y+w is 8.

In some embodiments, Z is methyl. In some embodiments, Z is a non-methyl group, as discussed hereinbelow.

In some embodiments, R$_1$ is hydrogen.

In some embodiments of Formula I, R$_1$ is an alkyl, optionally terminating with a carboxyl group, denoted —(CH$_2$)$_m$CO$_2$R$_7$, wherein the integer m ranges from 1 to 6 and R$_7$ is H (in cases of a carboxylic acid); or an alkyl, an aryl, a heteroaryl, an alicyclic or a heterocyclic (in cases of an ester). In some embodiments where R$_7$ is H, this compound can be converted into a salt readily, as exemplified in the Examples section that follows below (see, for example, a compound denoted TZD10AANa).

When considering the ABF compounds for various applications, their overall chemical attributes are considered, such as solubility, as well as their anti-biofilm formation activity. Hence, the ability to modify these compounds into salts provides, for example, for enhanced solubility of some ABF compounds in aqueous media. The modification of solubility can be achieved by other modifications, such as attachment to a soluble polymer entity (e.g., PEG), the introduction of heteroatoms in the long alkyl chain, and the introduction of solubility enhancing groups such as carboxyls and amines in various positions in the compound.

In some embodiments, X in Formula I is a heteroatom, such that the substituent is a alkylene chain interrupted by a heteroatom, as exemplified in the Examples section that follows (see, a compound denoted TZD1c). Such modification can, for example, improve the solubility of the compound.

One exemplary sub-family of compounds encompassed by general Formula I is represented by general Formula A1:

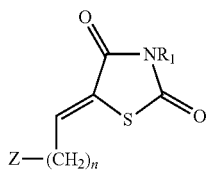

Formula A1 wherein A of Formula I is O and T of Formula I is S;

$R_1$ is H, alkyl or —$(CH_2)_mCO_2R_7$;

n is an integer which ranges from 7 to 20, and corresponds equivalently to y+w in Formula I and Formula A1, presented in the Examples section hereinbelow;

Z is H, —$CH_3$, —C(═O)Q, a linking moiety, a reactive group, a polymer moiety or a polymerizable moiety, as defined herein;

Q is —OH, —$OR_3$, —$NR_4R_5$ or —NHOH; and $R_3$, $R_4$, $R_5$ and $R_7$ are each independently H, alkyl or aryl.

Following are some exemplary anti-biofilm forming (ABF) compounds which belong to the sub-family referred to herein as thiazolidinediones (TZDs), according to embodiments of the present invention, the preparation of which can be found in the Examples section hereinbelow:

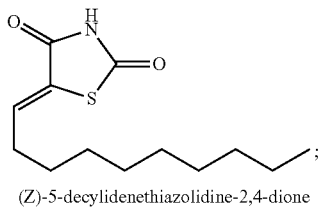

(Z)-5-decylidenethiazolidine-2,4-dione (TZD10)

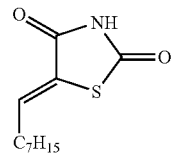

(Z)-5-octylidenethiazolidine-2,4-dione;

(TZD8)

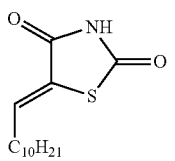

(Z)-5-undecylidenethiazolidine-2,4-dione;

(TZD11)

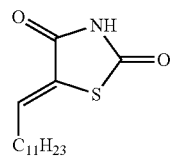

(Z)-5-dodecylidenethiazolidine-2,4-dione;

(TZD12)

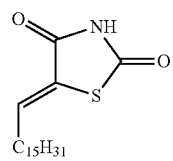

(Z)-5-hexadecylidenethiazolidine-2,4-dione;

(TZD16)

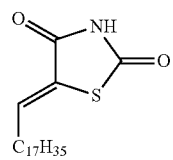

(Z)-5-octadecylidenethiazolidine-2,4-dione;

(TZD18)

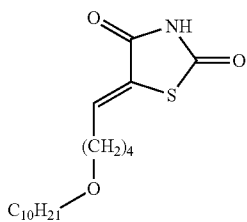

(Z)-5-(5-(decyloxy)pentylidene)thiazolidine-2,4-dione;

(TZD1c)

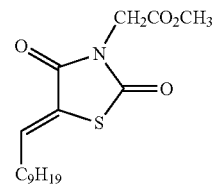

(Z)-methyl 2-(5-decylidene-2,4-dioxothiazolidin-3-yl)acetate;

(TZD10MA)

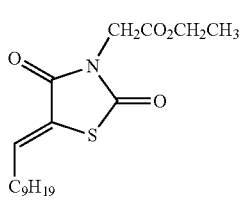

(Z)-ethyl 2-(5-decylidene-2,4-dioxothiazolidin-3-yl)acetatec;

(TZD10EA)

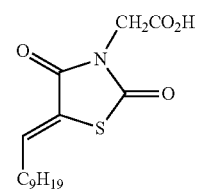

(Z)-2-(5-decylidene-2,4-dioxothiazolidin-3-yl)acetic acid; and (TZD10AA)

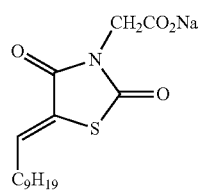

sodium (Z)-2-(5-decylidene-2,4-dioxothiazolidin-3-yl)acetate.

(TZD10AANa)

According to other embodiments of the present invention, compounds encompassed under Formula I, which belong to the sub-family of ABF compound referred to herein as pyrrole-2,5-diones (PYDs), include molecules represented by general Formula I, wherein T is $CH_2$.

In some embodiments, other variables of Formula I are the same as described hereinabove.

In some embodiments, A is O. In some embodiments, $R_1$ is H, alkyl or an alkyl terminated with a carboxyl group, denoted —$(CH_2)_m CO_2 R$, as defined herein.

In some embodiments, X is absent.

Exemplary PYD compound, wherein $R_1$ is H and Z is —$CH_3$, include, without limitations:

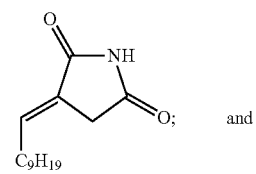

(E)-3-decylidenepyrrolidine-2,5-dione (PYD10)

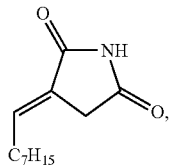

(E)-3-octylidenepyrrolidine-2,5-dione (PYD8)

the preparation of which is provided in the Examples section following below.

Similarly to the TZD subfamily, the alkyl substituent of compounds of the PYD family can be terminated by a non-methyl group, as detailed hereinbelow.

According to other embodiments of the present invention, compounds encompassed under Formula I, which belong to the sub-family of ABF compound referred to herein as imidazolidine-2,4-diones, include molecules represented by general Formula I, wherein T is NH.

In some embodiments, other variables of Formula I are the same as described hereinabove.

According to other embodiments of the present invention, compounds encompassed under Formula I, which belong to the sub-family of ABF compounds referred to herein as oxazolidine-2,4-diones, include molecules represented by general Formula I, wherein T is O.

In some embodiments, other variables of Formula I are the same as described hereinabove.

It is to be noted that for the sake of simplicity, in the general Formulae presented herein and in the definitions of some variables therein, non-substituted methylene groups, amine groups, and other groups are recited. The present embodiments, however, also encompass compounds in which these groups are substituted, even if not specifically indicated.

Thus, for example, when T is $CH_2$ (methylene), the methylene can be substituted by one or two substituents, as defined herein for an alkyl. When T is NH (amine), the amine can be similarly substituted.

As delineated hereinabove, the alkyl substituent of the heterocyclic core ring can be terminated by methyl or by a non-methyl group (denoted Z in the Formulae described herein).

A non-methyl Z group can be used to attach to the ABF compound other moieties, via variable chemical reactions.

Accordingly, Z can be a reactive group, such as, for example, a leaving group, being capable of participating in chemical reaction that results in attaching to the compound an additional moiety.

The phrase "reactive group", as used herein, describes a chemical group that is capable of undergoing a chemical reaction that typically leads to a bond formation. The bond, according to some embodiments, is a covalent bond. Chemical reactions that lead to a bond formation include, for example, nucleophilic and electrophilic substitutions, nucleophilic and electrophilic addition reactions, alkylation, addition-elimination reactions, cycloaddition reactions, rearrangement reactions and any other known organic reactions that involve bond formation between two reactants.

Non-limiting examples of reactive groups include amine, halo, hydroxyl, aldehyde, carbonyl, carboxyl, cyano, azide, nitro and the likes.

According to some embodiments, the reactive group on the ABF compound is located at the end of the long-alkyl chain, and is denoted Z in Formula I and Formula II.

For example, according to some embodiments, the reactive group which is capable of reacting with a compatible reactive group on a polymer moiety, comprises Z as a leaving group (such as halo), which can undergo an alkylation reaction (such as a nucleophilic substitution) with a corresponding reactive group on the polymer moiety.

As used herein, the phrase "leaving group" describes a labile atom, group or chemical moiety that readily undergoes detachment from an organic molecule during a chemical reaction, while the detachment is facilitated by the relative stability of the leaving atom, group or moiety thereupon. Typically, any group that is the conjugate base of a strong acid can act as a leaving group. Representative examples of suitable leaving groups according to the present embodiments therefore include, without limitation, halo, acetate, tosylate, triflate, sulfonate, azide, amine, hydroxy, thiohydroxy, alkoxy, cyanate, thiocyanate, nitro and cyano.

The term "acetate" refers to acetic acid anion.

The term "tosylate" refers to toluene-4-sulfonic acid anion.

The term "triflate" refers to trifluoro-methanesulfonic acid anion.

The term "azide" refers to an $N_3^-$.

The terms "hydroxy" and "thiohydroxy" refer to the $OH^-$ and $SH^-$ anions respectively.

The term "cyanate" and "thiocyanate" refer to $[O=C=N]^-$ and $[S=C=N]^-$ anions respectively.

The term "nitro" refers to $NO_2^-$.

The term "cyano" refers to $[C\equiv N]^-$.

In some embodiments, the leaving group is halo.

As used herein, the phrase "linking moiety" describes a chemical moiety or a group, which links the ABF compound presented herein to another chemical entity, such as a polymer or polymerizable moiety, or a surface of an object. The linking moiety can thus be, for example, formed upon reacting a reactive group which forms a part of other chemical entity with another reactive group which forms a part of the ABF compound.

For example, the reactive group on the side of the ABF compound can be an amine, and the reactive group on the side of a polymer moiety, as another chemical entity, may be a carboxyl group, and the linking moiety which forms therebetween is an amide. Similarly, a reaction between a hydroxyl and a carboxyl will lead to the formation of an ester linking moiety, and so on.

For another example, Z in Formula I is hydroxy or amine, as exemplified in Scheme 7 and Scheme 9 of Example 4 in the Examples section following below.

According to some embodiments of the present invention, the ABF agents presented herein are attached to another chemical entity, such as a polymer moiety or a polymerizable moiety (as defined hereinbelow), hence forming conjugates which include one or more ABF compounds as presented herein and one or more polymeric moieties. Such conjugates exhibit the ABF activity of the parent ABF compound as well as other attributes endowed by the polymeric moiety, such as hydrophobicity/hydrophilicity, surface tension/activity, and the ability to be incorporated in or on other substances as a polymeric coating layer. Hence, herein and throughout, the term "conjugate" refers to an ABF compound/agent which is conjugated to a polymer, or, in other word, have a polymer attached thereto.

The ABF agents can be conjugated with a polymer moiety or a polymerizable moiety via a linking moiety, as described hereinabove.

The phrase "polymerizable moiety", as used herein, refers to any moiety of a compound that can be polymerized, either spontaneously or as a result of a chemical or physical effect. A polymerizable moiety is synonymous with terms such as "monomer", "building block" and other terms used to describe chemical elements a plurality of which comprise a polymer. For example, an amino acid moiety relates to a peptide or a protein as a polymerizable moiety to a polymer; and a glucose moiety relates to starch similarly. As presented hereinbelow, an ABF compound can be tethered to a methacrylate monomer which can form a part of a methacrylate polymer, or polymethacrylate (see Example 4 in the Examples section that follows below).

In some embodiments, Z is a polymerizable group, which upon polymerization thereof, results in the ABF compound conjugated to the polymer.

In embodiments pertaining a ABF compound having a polymer attached thereto, the polymer moiety can be any polymer, and can be selected according to the intended use of the conjugate, as will be discussed hereinbelow. Non-limiting examples of polymers which can be used in the context of the present embodiments include polyacrylates, polymethacrylates, polyethylene glycols (PEGs), oligo/polysaccharides, aminoacids/peptides/proteins, nucleic acids, polyurethanes, epoxy resins, fluoropolymers, polyimides, polyamides, polyacrylamides, polyhydroxyethyl methacrylates, N-vinyl-2-pyrrolidinone and the likes.

Accordingly, non-limiting examples of a polymerizable moiety are groups forming the above-listed polymers once subjected to polymerization.

Optionally, in some embodiments, Z is a targeting moiety, which enables targeting the ABF to a location where a biofilm has been formed or is likely to be formed, as detailed hereinbelow.

According to embodiments of the present invention, the compounds and conjugates presented herein exert anti-biofilm formation activity. According to other embodiments, the compounds and conjugates presented herein exert ABF activity while substantially not exerting antimicrobial activity.

The term "biofilm", as used herein, refers to an aggregate of living cells which are stuck to each other and/or immobilized onto a surface as colonies. The cells are frequently embedded within a self-secreted matrix of extracellular polymeric substance (EPS), also referred to as "slime", which is a polymeric sticky mixture of nucleic acids, proteins and polysaccharides. Biofilms may form on living or non-living, organic or inorganic substrates, and constitute a prevalent mode of microbial life in natural, industrial and hospital settings.

In the context of the present embodiments, the living cells forming a biofilm can be cells of a unicellular microorganism (prokaryotes, archaea, bacteria, eukaryotes, protists, fungi, algae, euglena, protozoan, dinoflagellates, apicomplexa, trypanosomes, amoebae and the likes), or cells of multicellular organisms in which case the biofilm can be regarded as a colony of cells (like in the case of the unicellular organisms) or as a lower form of a tissue.

According to some embodiments of the present invention, the cells are of microorganism origins, and the biofilm is a biofilm of microorganisms, such as bacteria and fungi. The cells of a microorganism growing in a biofilm are physiologically distinct from cells in the "planktonic form" of the same organism, which by contrast, are single-cells that may float or swim in a liquid medium. Biofilms can go though several life-cycle steps which include initial attachment, irreversible attachment, one or more maturation stages, and dispersion. Major differences in protein expression of biofilm forming microorganisms in their sessile phase, compared to that of stationary-phase planktonic cells, make biofilms a completely different mode of microorganism, and one manifestation of this difference is the cells become resistant to a range of antibiotics and disinfectants.

The phrases "anti-biofilm formation activity" or "anti-quorum sensing activity", as these equivalent terms are used herein interchangeably, refer to the capacity of a substance to effect the prevention of formation of a biofilm of bacterial, fungal and/or other cells; and/or to effect a disruption and/or the eradication of an established and/or matured biofilm of bacterial, fungal and/or other cells; and/or to effect a reduction in the rate of buildup of a biofilm of bacterial, fungal and/or other cells on a surface of a substrate, be it an organic substrate of an inorganic substrate.

Hence, biofilms can form on an inanimate substrate or a living substrate. A well known case of a pathologic case of biofilm formation in a living subject, are streptococcal infections, which is the basis for the intense virulence of many streptococcal species. Such examples are discussed in details hereinbelow.

The phrases "anti-biofilm formation compound/conjugate/agent", "ABF compound/conjugate/agent", "anti-quorum sensing compound/conjugate/agent", "AQS compound/conjugate/agent", "quorum sensing inhibitor", "QSI" and "anti-biofouling compound/conjugate/agent", as these equivalent terms are used herein interchangeably, refer to a substance having an anti-biofilm formation activity, as defined herein.

In the context of the present invention, the phrase "ABF agent" does not mean necessarily an antimicrobial agent, and according to some embodiments of the present invention, the ABF agents are not considered anti-microbial agents. In the context of the present invention, a compound or agent which does not exhibit microbicidal (anti-microbial) activity (toxic to microorganisms) at a concentration lower than 10 mM is referred to herein as being non-toxic to microorganisms, and hence it is not an antimicrobial compound or agent, and is not a cytotoxic agent.

The phrases "cytotoxic agent" as used herein, refers to a substance that can effect death, eradication, elimination, reduction in number, reduction of growth rate, change in population distribution of one or more living cells of unicellular or multicellular life forms.

The phrase "anti-microbial agent" (antimicrobial agent) as used herein, refers to a substance that can effect death, eradication, elimination, reduction in number, reduction of growth rate, change in population distribution of one or more species of microbial life forms.

As discussed hereinabove, the ABF compounds and conjugates according to embodiments of the present invention, exert ABF activity and can thus prevent or reduce the formation or the mass of a biofilm, and/or disrupt an existing (established) biofilm. Therefore, the compounds and conjugates presented herein can be used in methods and compositions which are directed at anti-biofilm formation purposes, as detailed hereinbelow.

According to embodiments of the present invention, the activity of preventing or reducing the formation of a biofilm, and the activity of disrupting a biofilm which has been established before treatment, may be achieved by identical or different ABF agents. The prevention or reducing of forming a biofilm assumes that the biofilm has not yet been formed, and hence the presence of the ABF agent is required also in cases where no biofilm is present or detected. In other applications and embodiments, the biofilm has already been formed and the disruption thereof is desirable; thus in these cases the ABF agent according to embodiments of the present invention, may be introduced before, during or after the detection of presence of the biofilm.

As used herein, the term "preventing" in the context of the formation of a biofilm, indicates that the formation of a biofilm is essentially nullified or is reduced by at least 20% of the appearance of the biofilm in a comparable situation lacking the presence of the ABF agent. Alternatively, preventing means a reduction to at least 15%, 10% or 5% of the appearance of the biofilm in a comparable situation lacking the presence of the ABF agent. Methods for determining a level of appearance of a biofilm are known in the art.

As used herein, the term "disrupting" in the context of the formation of a biofilm, indicates that the mass of a biofilm is reduced to at least 20% of its mass prior to the introduction of the ABF agent presented herein. Alternatively, disrupting means a reduction in the mass of the biofilm to at least 30%, 40% or 50% of its original mass prior to the introduction of the ABF agent.

In some embodiments, disrupting a biofilm, or reducing a biofilm mass, results in converting at least a portion of the biofilm (e.g., at least 20%, 30%, 40%, 50%, 60%, 70%, 80%, 90% and even 100%) into planktonic cells that formed the biofilm.

According to some aspects of the present invention, there is provided a method of preventing or reducing a formation of a biofilm or of disrupting an existing (established) biofilm. The method can be effected in a living subject or on an inanimate object. The method is effected by contacting (e.g., applying or administering) the biofilm with an effective amount of the ABF compounds presented herein, as discussed in details hereinbelow.

For example, a method for preventing or reducing a formation of a biofilm or disrupting an established biofilm in a living subject, such as a subject suffering from a microbial (bacterial and/or fungal) infection, is effected by administering to the subject in need thereof a therapeutically effective amount of the ABF agent according to embodiments of the present invention.

Medical conditions that may be ameliorated by the use of the ABF agents presented herein, or compositions containing the same, according to embodiments of the present invention, include diseases and medical conditions involving a bacterial or fungal infection, and in particular an infection wherein the bacteria or fungi may form or already formed a biofilm. Typically these diseases effect organs which include ear, nose, throat, mouth, eye, lung, heart, kidney, gall bladder, pancreas, nervous system, skin, bone and the likes.

The administration of the effective amount of the ABF agent can be accompanied with a concomitant or sequential administration of a therapeutically effective amount of an antimicrobial agent, as described hereinbelow, thereby the antimicrobial affect of the antimicrobial agent is heightened as a result of preventing the formation and/or disrupting a biofilm of the infecting microorganism in the subject. Such synergism between the ABF agents presented herein, and many known antimicrobial agents can be effected by co-administration thereof.

The ABF agents presented herein can be highly effective when administered together with an antibiotic or antimicrobial agent, for eradicating pathogenic microorganisms which are more resistant to the antimicrobial agent due to the formation or the tendency of forming a biofilm. The ABF agents presented herein are capable of re-sensitizing the pathogenic microorganisms which formed a biofilm to the antimicrobial agent, such that when the microorganism is in its planktonic form, it is more sensitive to the co-administered antimicrobial agent.

The mode of administration can be topical or systemic, according to the desired therapeutic effect. For example, in a streptococcal infection, it may be sufficient to administer the ABF agent locally in the throat and over the larynx where biofilms of the bacteria may take hold. In more severe infections, it may be more effective to administer the ABF agent systemically.

The conjugates according to some embodiments presented herein can also be used in a method for preventing or reducing a formation of a biofilm or disrupting an established biofilm in a living subject. Such conjugates will be formed with polymer moieties which are suitable for therapeutic purposes. For example, the polymer can be used to target the infected tissue in the subject, as in the case of polymers such as an oligosaccharide, a peptide or an oligonucleotide, and thereby deliver the ABF agent to which it is conjugated to the exact location of the biofilm formed by the infectious microorganism. The polymer can also be targeted at the specific microorganism or to other substances secreted thereby to form the biofilm. For another example, the polymer can increase the solubility or physiological transportability of the ABF agent once administered to the subject, thereby controlling its pharmacokinetics in terms of absorption, distribution, metabolism and excretion of the ABF agent in the body of the subject.

The phrase "therapeutically effective amount" is used herein to describe an amount of a therapeutic agent being administered which will relieve to some extent one or more of the symptoms of the condition being treated thereby. For example, a therapeutically effective amount in the context of the aforementioned method using an ABF agent, is the amount that will effect the prevention or reduction of the formation of a biofilm or effect the disruption of an established biofilm formed by the pathogenic microorganism in the subject, as defined hereinabove. In the context of an antimicrobial agent, the therapeutically effective amount is the amount that will reduce or eradicate the microorganism.

The method of preventing or reducing a formation of a biofilm or disrupting a biofilm can be effected in an inanimate object or substrate, including systems (such as for containing and/or transporting and/or treating aqueous media or water), devices, containers, filters, tubes, solutions and gases and the likes, which are susceptible to biofilm formation or in which it desired to prevent biofilm formation. In such cases, the "effective amount" is defined as the amount which is sufficient to prevent or reduce the formation of a biofilm, or disrupt an established biofilm in the substrate. Such amounts may be different than the amounts used in therapeutic or pharmaceutical methods as the considerations of toxicity are different.

The method of preventing or reducing a formation of a biofilm or disrupting a biofilm in an inanimate object can be effected by dipping, spraying, coating, applying or otherwise contacting the object to be treated against biofouling with a solution of the ABF agent or a powder thereof.

In some embodiments, contacting the object to be treated is accompanied by concomitant or sequential contacting of the object with an anti-microbial agent, as discussed herein.

In general, "biofouling" is known as the undesirable accumulation of microorganisms, plants, algae, and animals on submerged or otherwise wet structures. Biofouling can also occur on the surfaces of living organisms. Biofouling is also found in membrane systems, such as membrane bioreactors and reverse osmosis spiral wound membranes. In the same manner it is found as fouling in cooling water cycles of large industrial equipments and power stations.

A common method for reducing cellular and proteinaceous fouling (also referred to as biofouling or biological fouling), is the immobilization of anti-biofouling compounds or agents to potentially infected surfaces, typically via the mediation of polymers which thereby constitute anti-biofouling polymers. Over the years several polymer classes have been explored for this purpose, including polyacrylates, oligosaccharides, polymer mimics of phospholipids, and polyethylene glycol (PEG).

Two basic strategies exist for functionalizing material surfaces with anti-biofouling polymers. The first approach, termed graft-to, consists of the adsorption to surfaces of presynthesized polymer chains end-functionalized with a chemical anchoring group. Alternatively, graft-from approaches, in which a polymer is grown in situ from the surface via a surface-adsorbed initiation group, are generally capable of producing denser polymer layers. Essential to both approaches, however, is the requirement of a robust mechanism for immobilizing the anti-biofouling polymer onto metals, ceramics, polymers, and electronic materials. Numerous methods of anchoring polymers to surfaces have been proposed, and can be broadly classified as either physisorptive or chemisorptive. Physisorption relies on relatively weak van der Waals and hydrophobic forces to tether polymers to a surface. Consequently, the polymers are not irreversibly bound to the surface and proteins may be exchanged with the polymer on the surface. To provide greater stability, anchoring strategies involving the formation of more robust chemical bonds between the polymer and surface are deemed more desirable, as exemplified by thiol-Au or silane-metal oxide interactions. More recently mimics of mussel adhesive proteins (MAPs) which rely on the 1,2-dihydroxyphenyl unit have been used successfully to anchor polymeric chains to metal surfaces.

Accordingly, the ABF agents of the invention maybe immobilized on a surface of an object by coating or direct immobilization thereof in the form of the conjugates of ABF agent and a polymer moiety or a polymerizable moiety, according to embodiments of the present invention.

Hence, according to another aspect of some embodiments of the present invention, there is provided a method of preventing the formation of a biofilm on a substrate, which is effected by applying to a surface of the substrate an effective amount of the conjugate presented herein, as defined hereinabove for use of the un-conjugated ABF agents as used with conjunction to inanimate objects.

The aforementioned method for fighting biofouling can be effected by spraying or otherwise applying a conjugate of an ABF compound and a polymerizable moiety, and allowing/effecting its polymerization on the surface of the substrate. Alternatively the pre-formed polymer conjugate can be applied onto the surface, and further alternatively, the polymer may be already applied and attached to the surface of the substrate and the ABF agent is conjugated thereto in situ.

In any of the methods presented hereinabove, the ABF agent or conjugate can be formulated as a composition suitable, packaged and identified for any particular use thereof.

Hence, according to another aspect of the present invention, there is provided a composition containing the ABF agent presented herein as an active ingredient, and a compatible carrier. Such a composition can therefore be used in the method of preventing or reducing a formation of a biofilm or of disrupting a biofilm.

Such composition can also be packaged in a packaging material and identified in print, in or on the packaging material, for use in a method of preventing or reducing a formation of a biofilm or disrupting a biofilm.

The ABF agent can be formulated in a composition as the only active ingredient. Alternatively, such composition can also include one or more additional active ingredients which can act along side or synergistically with the ABF agents, according to the intended use of the composition.

In some embodiments, the additional active ingredient(s) can be packaged together with the ABF agent or each individually, according to the intended use and storage conditions. When packaged separately, the two active ingredients can be mixed together prior to use, or administered/applied concomitantly or sequentially, according to the intended use.

For example, the composition can be a pharmaceutical composition and the carrier is a pharmaceutically acceptable carrier. Such a pharmaceutical composition is intended for the treatment of a disease or condition wherein a beneficial effect may be achieved by juxtaposing an ABF agent and an anti-microbial agent, the first prevents and/or disrupts the biofilm protecting the pathogen from the antimicrobial agent, and the latter delivers the killing effect to the pathogen.

As used herein a "pharmaceutical composition" refers to a preparation of one or more of the ABF agents described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the ABF agents into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert.

Compositions comprising an ABF agent of the present invention formulated in a compatible pharmaceutical carrier may also be prepared, placed in an appropriate container, and labeled for treatment of a particular medical condition, disease or disorder, as is detailed hereinabove.

Hence, according to other embodiments, the pharmaceutical composition is being packaged in a packaging material and identified in print, in or on the packaging material for use in the treatment of a medical condition in which reducing, preventing or disrupting a biofilm in a subject is beneficial, as these are discussed hereinabove.

Accordingly, there is provided a use of the ABF agent as presented herein in the manufacture of a medicament for treating a disease or disorder in which reducing or preventing the formation of a biofilm and/or disrupting a biofilm in a subject is beneficial.

Further, the medicament, or pharmaceutical compositions presented herein may include an antimicrobial agent as an additional active ingredient, such that a synergistic antimicrobial effect is obtained therefrom.

Non-limiting examples of an antimicrobial agents which are suitable for use in the medicaments or pharmaceutical compositions presented herein include, without limitations, antimicrobial peptides, antimicrobial glycopeptides, antimicrobial aminoglycosides, amoxicillin, ampicillin, azithromycin, cefonicid, cefotetan, cephalosporin, cephamycin, chlortetracycline, ciprofloxacin, clarithromycin, clindamycin, cycloserine, dalfopristin, doxycycline, ephalothin, erythromycin, gentamycin, kanamycin, levofloxacin, lincosamide, linezolid, moxifloxacin, mupirocin, neomycin, oxytetracycline, penicillin, quinupristin, rifampicin, spectinomycin, streptomycin, sulfanilamide, trimethoprim and vancomycin and any derivatives thereof.

As mentioned above, the additional antimicrobial agent for co-administration with an ABF agent according to embodiments of the present invention can be packaged together with the ABF agent or separately.

The ABF agents presented herein can be used as an active ingredient in compositions which are not meant for pharmaceutical use, such as compositions for disinfecting and rinsing of inanimate objects and surfaces, as well as for external use on the body of living subjects. Also in these compositions an additional active ingredient can be used, such as an antimicrobial agent (not necessarily a pharmaceutical agent), which is effective against microorganisms in their planktonic form, and the active ingredients can be packaged together or individually, according to the intended use and storage conditions.

The conjugates presented herein can be used as anti-biofouling compositions. For example, the ABF or anti-biofouling compounds presented herein, such as the exemplary TZD10 and other TZDs presented hereinbelow, can be attached to various polymers to form conjugates, and these conjugates can be used as an active ingredient in various compositions.

Compositions containing an ABF conjugate as an active ingredient can be packaged in a packaging material and identified for use in a method of preventing a formation of a biofilm on a substrate.

For example, an anti-biofouling composition, according to embodiments of the present invention, can include polymers which are suitable for coating a surface, namely polymers which form a solid or semi-solid layer when applied over a surface of a substrate. These polymers are used as the polymer moiety in the conjugates presented herein, thereby forming an ABF layer which will protect the substrate from microorganisms' biofilm formation, development and buildup thereon.

For another example, the ABF agents presented herein can form conjugates with polymer moieties which are suitable for spraying and inkjet printing techniques. Such polymers are found as dispersions in a liquid media, and once applied and cured onto a surface of a substrate, such as a solid material, semi-solid surface, absorptive surface, and even skin, hair, feathers or fur, form a thin layer which can be tailored to be flexible or rigid, depending on the type and amount of the applied polymer.

Anti-biofouling compositions which include as an active ingredient the conjugates based on such polymer moieties will endow ABF protection to the substrate they are applied on. In particular the anti-biofouling compositions presented herein may be used for preventing or disruption formation of biofilm on medical devices such as various implants, pace makers, stents, artificial joints, catheters, implants for directing and controlling the flow of body fluids, implants for dialysis and the likes. Another beneficial use for such anti-biofouling compositions is in water treatment systems, which include pipes and tubes, valves, filters, fittings, seals, reservoirs and basins, all of which are susceptible to biofouling and thus all of which can be treated with the compositions presented herein to prevent biofouling therein and/or thereon.

The anti-biofouling compositions, in some embodiments, can include an ABF compound, as described herein, and a polymer moiety, as described herein, packaged separately. The ABF compound has a reactive group which is compatible to a reactive group of the polymer, as discussed hereinabove, and composition is applied on a surface of a substrate by first applying the polymer and then conjugating thereto the ABF compound by means of bond formation between the reactive groups.

According to embodiments of the present invention, the compositions provided herein can be packaged and identified for various uses, taking various forms according to the desired form of contacting the ABF agent with the substrate. The compositions containing the ABF agent presented herein can be used to enhance or effect the disinfection of various vessels, systems, devices, surfaces, tools, hulls and areas. For example, the composition can be in a form of a spray applicator for spraying the composition for preventing and/or reducing and/or disrupting a biofilm on the sprayed surface of the substrate. Alternatively, the composition may be in a form of an immersion solution, a scrubbing solution, a paste or powder, which is used for removal and forestallment of a biofilm from a surface of a substrate.

The ABF agent can therefore be applied to any surface where biofilm may form or already formed, such as substrates made of a mineral (rock or glass), organic material (wood, wool, silk, cotton, hemp, leather, fur, feather, skin, hide, pelt or pelage), metal, plastic, woven or knitted fabrics and any combinations thereof.

In the case of a pharmaceutical composition, the mode of treatment and the type of medical condition may dictate a liquid syrup or a tablet form for local or systemic administration of the ABF agent. Alternatively, the ABF agent may be administered as a spray for inhalation, which can be in a powder or a mist of a liquid form.

Another aspect the present invention concerns the use of the ABF agents for harvesting live cells from an established biofilm. For example, when a sample of the microorganism in the biofilm form is required for analysis and identification, but mechanical sampling cannot be accomplished due to an inaccessible location of the biofilm, the detachment of living cells in their planktonic form can be effected chemically by the ABF agents presented herein.

Hence, according to another aspect of the present invention, there is provided a method for harvesting living cells from a biofilm, which is effected by contacting the biofilm with an effective amount of an ABF agent presented herein, thereby disrupting the biofilm and releasing living cells therefrom in their planktonic form, followed by collecting the cells.

It is expected that during the life of a patent maturing from this application many relevant anti-biofilm agents will be developed and the scope of the phrase "anti-biofilm agent" is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Example 1

Material and Methods 2,4-Thiazolidinedione was obtained from Meryer Chemical and Fluka chemicals Aldehydes were obtained from Sigma Aldrich, Alfa Aesar and SAFC Maleimide was obtained from Sigma Aldrich and Alfa Aesar Solvents was obtained from Biolab, J.T. Baker Structure analyses were performed on an NMR-300 Hz by Varian.

Chemical Syntheses

The compounds below refer to a novel family of compounds according to some embodiments of the present invention, having the general Formula I:

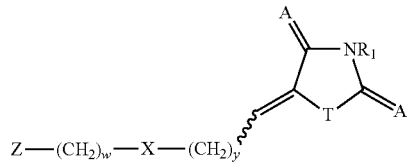

Formula I wherein the variables in Formula I are as follows:
A is selected from the group consisting of O, S and $R_{10}$;
T can be —S—, —O—, —CH$_2$— or NR$_6$—;
$R_1$ can be H, alkyl, aryl, heteroaryl, alicyclic, heterocyclic or —(CH$_2$)$_m$CO$_2$R$_7$;
m is an integer equal or greater than 1;
y and w are integers, the sum of which is greater than or equal to 7;
X can be —CH$_2$—, —CR$_8$R$_9$—, —O—, —S—, —NR$_2$— or absent;
Z can be H, —CH$_3$, —C(=O)Q, a linking moiety, a reactive group, a polymer moiety or a polymerizable moiety, as defined herein;

Q can be —OH, —OR$_3$, —NR$_4$R$_5$ or —NHOH;

R$_2$, R$_3$, R$_4$, R$_5$, R$_6$, R$_7$, R$_8$, R$_9$ and R$_{10}$ can each be independently H, alkyl, aryl, heteroaryl, alicyclic or heterocyclic; and any hydrate, solvate or salt thereof The following are general and specific procedures for the preparation of various exemplary sub-families, varying by the T group, of compounds encompassed by Formula I.

Synthesis of Long-Chain Thiazolidinedione Derivatives

General Procedure A

The general procedure for the reaction between a thiazolidinedione ring (TZD) and a long-chain aldehyde, presented in Scheme 1 below, is used to produce a double bond.

2,4-Thiazolidinedione (1 equivalent) is added to a solution of a long-chain aldehyde (about 0.85 equivalents) in ethanol in the presence of catalytic amount of piperidine at room temperature. The reaction is kept for about 24 hours at 80-90° C. and then cooled to 0° C. in an ice bath. Thereafter 1 N HCl and water are added and the precipitate is filtered on a sinter glass filter, washed with water and petroleum ether and dried in vacuum to obtain an analytically pure TZD derivative compound.

Scheme 1

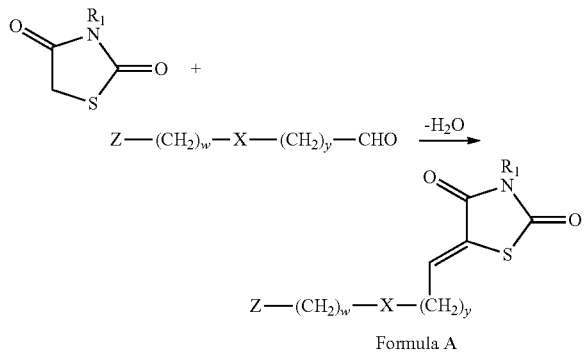

Formula A

The variables in Formula A in Scheme 1 are as follows:

R$_1$ can be H, alkyl, aryl, heteroaryl, alicyclic, heterocyclic and —(CH$_2$)$_m$CO$_2$R$_7$ whereas m is an integer greater than 1;

y and w are integers, the sum of which is greater than or equal to 6;

X can be —CH$_2$—, —CR$_8$R$_9$—, —O—, —S— or —NR$_2$—;

Z can be H, —CH$_3$ or —C(=O)Q;

Q can be —OH, —OR$_3$, —NR$_4$R$_5$ or —NHOH; and

R$_2$, R$_3$, R$_4$, R$_5$, R$_7$, R$_8$ and R$_9$ can each be independently H, alkyl, aryl, heteroaryl, alicyclic or heterocycli Formula A also encompasses metal or ammonium salts of the compounds encompassed thereby, as defined herein.

This reaction between 2,4-thiazolidinedione and a variety of long-chain aldehydes was employed to prepare a series of long-chain TZD derivatives, which were examined in preliminary activity assays as anti-biofilm formation (ABF) agents, as presented hereinbelow. Such ABF compounds can be represented as a subgenus of Formula A, namely Formula A1:

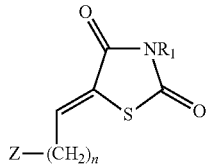

Formula A1 wherein:

R$_1$ is selected from the group consisting of H, alkyl and —(CH$_2$)$_m$CO$_2$R$_7$;

n is an integer which ranges from 7 to 20, and corresponds equivalently to y+w in Formula I and Formula A hereinabove and throughout;

Z is selected from the group consisting of H, —CH$_3$, —C(=O)Q, a linking moiety, a reactive group, a polymer moiety and a polymerizable moiety, as defined herein;

Q is selected from the group consisting of —OH, —OR$_3$, —NR$_4$R$_5$ and —NHOH; and R$_3$, R$_4$, R$_5$ and R$_7$ are each independently selected from the group consisting of H, alkyl and aryl.

The protocol is slightly modified when preparing amine-containing derivatives. The structure of the compounds is determined by NMR and MS and compounds' purity is determined by microanalysis. Compounds of 98% and higher purity are used for activity assays.

Synthesis of (Z)-5-decylidenethiazolidine-2,4-dione (TZD10)

TZD10 was prepared according to General Procedure A presented hereinabove.

Specifically, 2,4-thiazolidinedione (thiazolidine-2,4-dione, 7.95 mmol) was added to a solution of decanal (6.64 mmol) in ethanol (22 ml) in the presence of catalytic amount of piperidine (0.2 ml) at room temperature.

Scheme 2

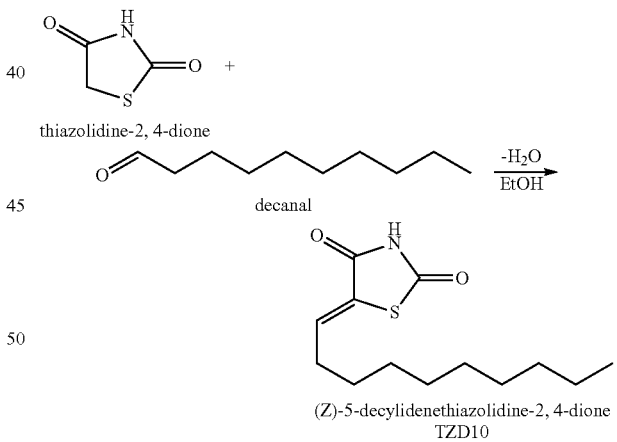

After heating for 24 hours at 80° C., the reaction mixture was cooled to 0° C. in an ice bath and thereafter 1 N HCl (0.2 ml) and H$_2$O (22 ml) were added and the yellow precipitate was filtered, washed with H$_2$O (30 ml) then with petroleum ether and dried under vacuum to obtain the pure compound TZD10 as white powder (yield about 75%).

m.p. 76-78° C. at 1 mm Hg.

$^1$H NMR (300 MHz, CDCl$_3$): δ=0.85 (t, JH,H=6.6 HZ, 3 H), 1.25 (s, 12H), 1.56 (m, 2H), 2.20 (q, JH,H=7.2 HZ, 2H), 7.05 (t, JH,H=7.5 HZ, 1H) ppm.

$^{13}$C NMR (75.9 MHz, CDCl$_3$): δ=14.33, 22.87, 28.04, 29.43, 29.46, 29.50, 29.64, 32.08, 126.48, 140.03, 166.03, 167.78 ppm.

Synthesis of (Z)-5-hexylidenethiazolidine-2,4-dione (TZD6)

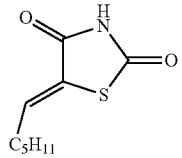

(Z)-5-hexylidenethiazolidine-2,4-dione

TZD6 was prepared according to General Procedure A presented hereinabove and similarly as presented for TZD10, using 2,4-thiazolidinedione and hexanal as reactants.

$^1$H NMR (500 MHz): δ=0.87 (t, 3H, $J_{HH}$=6.5 Hz), 1.34-1.36 (m, 4H), 1.36-1.56 (m, 2H), 2.21-2.26 (q, 2H $J_{HH}$=7.5 Hz), 7.06 (t, 1H, $J_{HH}$=7.5 Hz) ppm.

Synthesis of (Z)-5-octylidenethiazolidine-2,4-dione (TZD8)

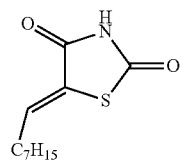

(Z)-5-octylidenethiazolidine-2,4-dione

TZD8 was prepared according to General Procedure A presented hereinabove and similarly as presented for TZD10, using 2,4-thiazolidinedione and octanal as reactants.

m.p. 72-74° C. at 1 mm Hg;

$^1$H NMR (500 MHz): δ=0.90 (t, 3H, $J_{HH}$=6 Hz), 1.29-1.34 (m, 8H), 1.53-1.57 (m, 2H), 2.21-2.25 (q, 2H $J_{HH}$=7.5 Hz), 7.06 (t, 1H, $J_{HH}$=8 Hz) ppm.

Synthesis of (Z)-5-undecylidenethiazolidine-2,4-dione (TZD11)

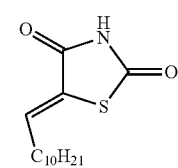

(Z)-5-undecylidenethiazolidine-2,4-dione

TZD11 was prepared according to General Procedure A presented hereinabove and similarly as presented for TZD10, using 2,4-thiazolidinedione and undecanal as reactants.

m.p. 72-73° C. at 1 mm Hg;

$^1$H NMR (300 MHz): δ=0.88 (t, 3H, $J_{HH}$=6.9 Hz), 1.26 (s, 14H), 1.45-1.55 (m, 2H), 2.19-2.25 (q, 2H $J_{HH}$=7.5 Hz), 7.04 (t, 1H, $J_{HH}$=7.8 Hz) ppm.

Synthesis of (Z)-5-dodecylidenethiazolidine-2,4-dione (TZD12)

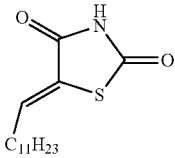

(Z)-5-dodecylidenethiazolidine-2,4-dione

TZD12 was prepared according to General Procedure A presented hereinabove and similarly as presented for TZD10, using 2,4-thiazolidinedione and dodecanal as reactants.

$^1$H NMR (300 MHz): δ=0.88 (t, 3H, $J_{HH}$=6.6 Hz), 1.26 (s, 16H), 1.49-1.56 (m, 2H), 2.17-2.25 (q, 2H $J_{HH}$=7 Hz), 7.04 (t, 1H, $J_{HH}$=7.8 Hz) ppm.

Synthesis of (Z)-5-hexadecylidenethiazolidine-2,4-dione (TZD16)

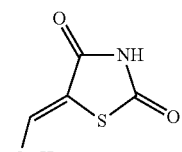

(Z)-5-hexadecylidenethiazolidine-2,4-dione

TZD16 was prepared according to General Procedure A presented hereinabove using 2,4-thiazolidinedione and palmitaldehyde as reactants.

$^1$H NMR (300 MHz, CDCl$_3$): δ=0.85 (t, $J_{H,H}$=6.6 Hz, 3H), 1.25 (s, 24H), 1.47 (m, 2H), 2.20 (q, $J_{H,H}$=6.2 Hz, 2H), 7.00 (t, $J_{H,H}$=7.5 Hz, 1H);

M.S: m/z=339;

Chemical analysis for $C_{21}H_{37}NO_2S$, calculated: C, 67.26; H, 9.72; N, 4.128; S, 9.45. found: C, 67.07; H, 9.77; N, 4.16; S, 9.51.

Synthesis of (Z)-5-octadecylidenethiazolidine-2,4-dione (TZD18)

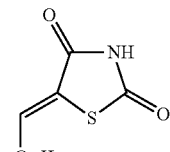

(Z)-5-octadecylidenethiazolidine-2,4-dione

TZD18 was prepared according to General Procedure A presented hereinabove using 2,4-thiazolidinedione and stearaldehyde as reactants.

m.p.: 97-98.5° C. at 1 mm Hg.

$^1$H NMR (300 MHz, CDCl$_3$): δ=0.87 (t, J$_{H,H}$=6.6 Hz, 3H), 1.25 (s, 28H), 1.53 (m, 2H), 2.21 (q, J$_{H,H}$=7.2 Hz, 2H), 7.05 (t, J$_{H,H}$=7.5 Hz, 1H);

M.S: m/z=367;

Chemical analysis for C$_{21}$H$_{37}$NO$_2$S, calculated: C, 68.67; H, 10.07; N, 3.81; S, 8.72. found: C, 68.22; H, 10.08; N, 3.79; S, 8.67.

Synthesis of (Z)-5-(5-(decyloxy)pentylidene)thiazolidine-2,4-dione (TZD1c)

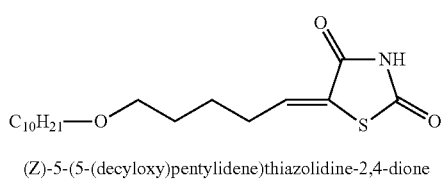

(Z)-5-(5-(decyloxy)pentylidene)thiazolidine-2,4-dione

TZD1c was prepared according to General Procedure A presented hereinabove, using 2,4-thiazolidinedione and 5-(decyloxy)pentanal as reactants.

$^1$H NMR (300 MHz, CDCl$_3$): δ=0.88 (t, J$_{H,H}$=3 Hz, 3H), 1.26 (s, 14H), 1.57 (s, 6H), 2.50 (m, 2H), 3.39 (m, 4H), 6.06 (t, J$_{H,H}$=9 Hz, 1H);

M.S: m/z=341.

Synthesis of N-Substituted Long-Chain Thiazolidinedione Derivatives

General Procedure A2

Compounds of Formula I wherein A is O, R$_1$ is alkyl, aryl, heteroaryl, alicyclic, heterocyclic or —(CH$_2$)$_m$CO$_2$R$_7$, wherein m is an integer equal to or greater than 1, which can be represented by a subgenus under Formula A2, are prepared according to General Procedure A2 illustrated in Scheme 3 below.

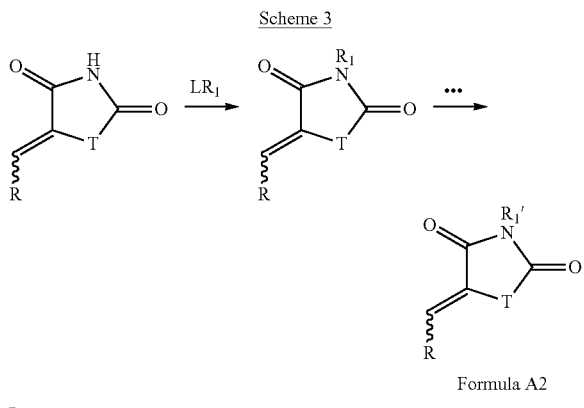

Formula A2

R = Z—(CH$_2$)$_w$—X—(CH$_2$)$_y$-

A precursor compound wherein the ring nitrogen is unsubstituted is made with the desired R group as presented hereinabove in General Procedure A, and is then reacted with a reagent being substantially composed of the desired R$_1$ group and a leaving group, to thereby afford the substitution of the ring nitrogen with R$_1$, and thereafter some workup may be performed to further modify R$_1$ to R$_1$'.

Following is the use of General Procedure A2 for the preparation of 5-alkyl-2,4-thiazolidinedione-3-acetates (2), partially adopted from Bruno G. et al., *Bioorg. Med. Chem.*, 10 (2002) 1077-1084.

Potassium hydride (0.432 grams, 10.8 mmol) is added in portions to a solution of 5-alkylidene-2,4-thiazolidinedione (9 mmol) in dry DMF (20 ml) and the mixture is stirred at 80° C. for 1.5 hours. The mixture is cooled to room temperature and a solution of methyl bromoacetate (1.54 grams, 10 mmol) in dry DMF is added dropwise, and the reaction mixture is stirred at 80° C. for 24 hours. Thereafter, the reaction mixture is cooled to room temperature and poured into H$_2$O. The solid byproduct is filtered, the filtrate is extracted with EtOAc and H$_2$O, the organic fractions are combined and evaporated to give a white product.

Exemplary compounds have been prepared following General Procedure A2 as presented below.

Synthesis of ((Z)-methyl 2-(5-decylidene-2,4-dioxothiazolidin-3-yl)acetate (TZD10MA)

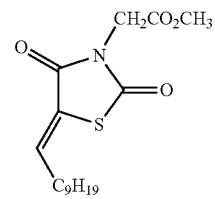

(Z)-methyl2-(5-decylidene-2,4-dioxothiazolidin-3-yl)acetate

TZD10MA was prepared according to General Procedure A2 presented hereinabove using (Z)-5-decylidenethiazolidine-2,4-dione and methyl bromoacetate.

Specifically, potassium hydride (0.432 grams, 10.8 mmol) was added portionwise to a solution of 5-alkylidene-2,4-thiazolidinedione (9 mmol) in dry DMF (20 ml) and the mixture was stirred at 80° C. for 1.5 hours. The mixture was cooled to room temperature and a solution of methyl bromoacetate (1.54 grams, 10 mmol) in dry DMF was added dropwise. After being stirred at 80° C. for 24 hours, the reaction mixture cooled to room temperature and poured into H$_2$O. The solid byproduct was filtrated, the filtrate was extracted with EtOAc and H$_2$O, the organic fractions were combined and evaporated to afford the product as a white powder.

Melting point: 30° C. at 1 mm Hg;

$^1$H NMR (300 MHz, CDCl$_3$): δ=0.88 (3H, t, J$_{H,H}$=6.9 Hz), 1.27 (14H, s), 2.21-2.28 (2H, o), 3.78 (3H, s), 4.43 (2H, s), 7.13 (1H, t, J$_{H,H}$=7.8 Hz) ppm;

$^{13}$C NMR (75 MHz, CDCl$_3$): δ=14.07, 22.61, 27.79, 29.18, 29.20, 29.24, 29.37, 31.79, 31.83, 41.65, 52.80, 124.64, 139.99, 164.25, 166.77, 167.33 ppm.

Synthesis of (Z)-ethyl 2-(5-decylidene-2,4-dioxothiazolidin-3-yl)acetate (TZD10EA)

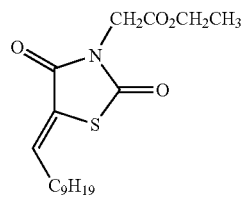

(Z)-ethyl 2-(5-decylidene-2,4-dioxothiazolidin-3-yl)acetate

TZD10EA was prepared according to General Procedure A2 presented hereinabove using (Z)-5-decylidenethiazolidine-2,4-dione and ethyl 2-bromoacetate as reactants.

$^1$H NMR (300 MHz, CDCl$_3$): δ=0.88 (3H, t, J$_{H,H}$=Hz), 1.27 (14H, s), 2.21-2.28 (2H, o), 3.78 (3H, s), 4.43 (2H, s), 7.13 (1H, t, J$_{H,H}$=Hz) ppm;
$^{13}$C NMR (75 MHz, CDCl$_3$): δ=14.07, 22.61, 27.79, 29.18, 29.20, 29.24, 29.37, 31.79, 31.83, 41.65, 52.80, 124.64, 139.99, 164.25, 166.77, 167.33 ppm.

Synthesis of (Z)-2-(5-decylidene-2,4-dioxothiazolidin-3-yl)acetic acid (TZD10AA)

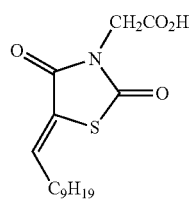

(Z)-2-(5-decylidene-2,4-dioxothiazolidin-3-yl)acetate acid

TZD10AA was prepared from TZD10EA presented hereinabove by mixing TZD10AA (5 mmol), glacial AcOH (20 ml) and HCl 12 N (5 ml) under reflux for 2 hours. Thereafter AcOH (20 ml) and HCl (5 ml) were added and refluxed for additional 2 hours. Extraction with EtOAc followed and the organic fractions were combined and evaporated under reduced pressure. The product was recrystallized from petroleum ether to afford TZD10AA at a yield of 65%.

$^1$H NMR (300 MHz, CDCl$_3$): δ=0.88 (3H, t, J$_{H,H}$=Hz), 1.27 (14H, s), 1.52-1.57 (H, o), 2.21-2.28 (2H, o), 4.48 (2H, s), 7.14 (1H, t, J$_{H,H}$=Hz) ppm;
$^{13}$C NMR (75 MHz, CDCl$_3$): δ=14.09, 22.62, 27.78, 29.19, 29.21, 29.24, 29.37, 31.80, 31.87, 41.41, 124.48, 140.37, 164.16, 167.27, 171.86 ppm.

Synthesis of sodium (Z)-2-(5-decylidene-2,4-dioxothiazolidin-3-yl)acetate (TZD10AANa)

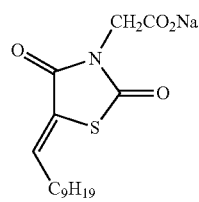

sodium (Z)-2-(5-decylidene-2,4-dioxothiazolidin-3-yl)acetate

TZD10AANa is an exemplary salt of an ABF compound according to embodiments of the present invention, wherein the salt is a sodium salt of TZD10AA which was prepared as presented hereinabove. A solution of TZD10AA (1 equivalent) in MeOH was added portionwise to a solution of sodium (1 equivalent) in MeOH and the mixture was stirred for 10 minutes. The mixture was evaporation to dryness under reduced pressure to afford TZD10AANa.

Synthesis of Long-Chain 4-Substituted-Maleimide Derivatives

General Procedure B

The general procedure for the reaction between a maleimide derivative (pyrrole-2,5-dione derivative) ring (PYD) and a long-chain aldehyde, based on a Wittig reaction of the maleimide-phosphorus glide obtained from the addition of triphenylphosphine to the maleimide derivative, followed by reaction with a long chain aldehyde which may or may not be substituted, is presented in Scheme 4 below.

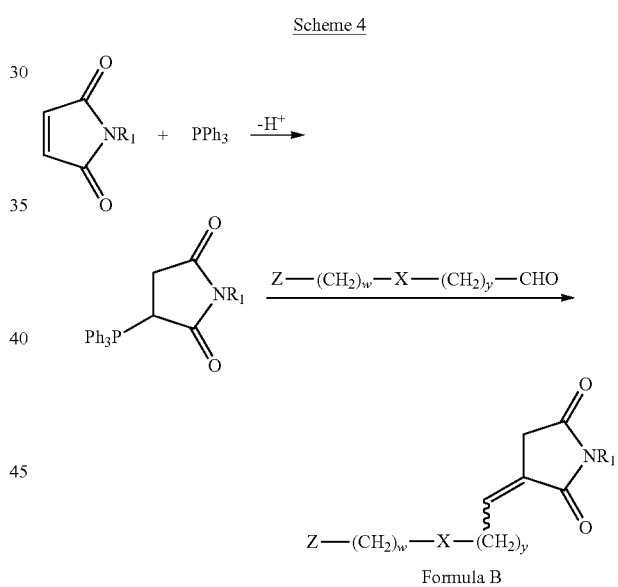

Scheme 4

Formula B

The variables in Formula B in Scheme 4 are as follows:

$R_1$ can be H, alkyl, aryl, heteroaryl, alicyclic, heterocyclic or —(CH$_2$)$_m$CO$_2$R$_7$, wherein m is an integer equal or greater than 1;

y and w are integers, the sum of which is greater than or equal to 8;

X can be —CH$_2$—, —O—, —S— or —NR$_2$—;

Z can be H, —CH$_3$ or —C(=O)Q;

Q can be —OH, —OR$_3$, —NR$_4$R$_5$ or —NHOH; and $R_2$, $R_3$, $R_4$ and $R_5$ can each be independently H, alkyl, aryl, heteroaryl, alicyclic or heterocycli This reaction between the PYD ring and a variety of long-chain aldehydes was employed to prepare several long-chain PYD derivatives.

Synthesis of (E)-3-decylidenepyrrolidine-2,5-dione (PYD10)

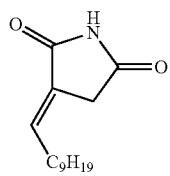

(E)-3-decylidenepyrrolidine-2,5-dione (E)-3-decylidenepyrrolidine-2,5-dione (PYD10) was prepared according to General Procedure B presented hereinabove.

Maleimide (0.1994 grams, 2 mmol) and triphenyl phosphine (0.5232 grams, 1.994 mmol) are mixed and refluxed for 1 hour in acetone (about 10 ml). A precipitate was obtained which was washed with several portions of acetone and then dried under reduced pressure to yield 100%.

The above product (2 mmol) and decanal (0.377 ml, 2 mmol) are mixed in methanol (10 ml) and refluxed for 12 hours. Thereafter the reaction mixture was cooled and HCl (1 N, 0.03 ml and water 10 ml) were added. The precipitate was filtered and washed with petroleum ether and purified by flash chromatography (silica, ethyl acetate: petroleum ether, 30:70) to afford pure PYD10.

FIG. 1 presents the $^1$H NMR spectra of PYD10.

Synthesis of (E)-3-octylidenepyrrolidine-2,5-dione (PYD8)

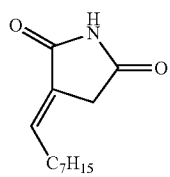

(E)-3-octylidenepyrrolidine-2,5-dione

PYD8 was prepared according to General Procedure B presented hereinabove.

A mixture of maleimide (0.2 grams, 2 mmol), triphenylphosphine (0.52 grams, 2 mmol), and acetone (3 ml) was heated under reflux for 1 hour. After cooling, the resulting precipitate was filtered, washed with acetone, and dried under reduced pressure.

Without further purification, the octanal (2 mmol) and methanol (5 ml) were added and the mixture was heated under reflux overnight, then cooled to 0° C., and quenched with HCl 1N (0.1 ml) and 10 ml water. The product was extracted with ether and purified on silica gel (petroleum ether, ethyl acetate).

m.p.: 78-80° C. at 1 mm Hg;

$^1$H NMR (300 MHz, CDCl$_3$): δ=0.87 (3H, t, $J_{H,H}$=6 Hz), 1.28 (8H, s), 1.46-1.51 (2H, o), 2.13-2.2 (2H, o), 3.25 (2H, s), 6.82 (1H, t, $J_{H,H}$=7.8 Hz), 8.01 (1H, s) ppm;

$^{13}$C NMR (75 MHz, CDCl$_3$): δ=13.61, 22.17, 27.66, 28.63, 28.82, 29.45, 31.28, 32.45, 126.40, 138.98, 170.64, 175.22 ppm.

The compounds below refer to another family of novel anti-biofilm formation compounds according to some embodiments of the present invention, having the general Formula II:

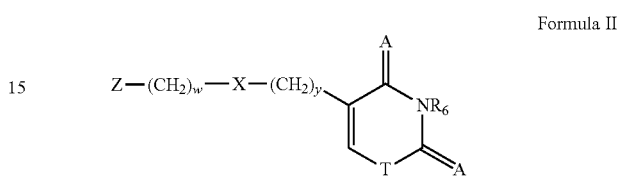

Formula II wherein the variables in Formula II are as follows:

A is selected from the group consisting of O, S and R$_{10}$;

Z is selected from the group consisting of H, —CH$_3$, —C(=O)Q, a linking moiety, a reactive group, a polymer moiety and a polymerizable moiety, as defined herein;

X is selected from the group consisting of —CH$_2$—, —CR$_8$R$_9$—, —O—, —S— and —NR$_2$— or absent;

y and w are integers, whereas y+w ranges from 7 to 20;

Q is selected from the group consisting of —OH, —OR$_3$, —NR$_4$R$_5$ and —NHOH;

T is selected from the group consisting of —S—, —O—, —CH$_2$—, —NR$_6$— and —NR$_7$—; and R$_2$, R$_3$, R$_4$, R$_5$, R$_6$, R$_7$, R$_8$, R$_9$ and R$_{10}$ are each independently selected from the group consisting of H, alkyl, aryl, heteroaryl, alicyclic and heterocycli The following are general and specific procedures for the preparation of various exemplary sub-families, varying by the T group, and all pertain to the family of Formula II.

Synthesis of Long-Chain 5-Substituted-Pyrimidine-2,4-Dione Derivatives

General Procedure C

The general procedure for the reaction for obtaining long-chain derivatives of 5-substituted-pyrimidine-2,4-dione (PMD), encompassed by Formula II, is illustrated in Scheme 5 hereinbelow.

A long chain ester, which may or may not be substituted, is lithiated with two equivalents of lithium diisopropylamide (LDA) in order to from two equivalents each of diisopropylamine and n-butyllithium, and thereafter reacted with ethylformate in THF at −78° C. Thereafter the ester of the 2-alkyl-3-oxopropanoate is treated with urea or an N,N'-disubstituted urea derivative to obtain a long-chain PMD derivative.

Scheme 5

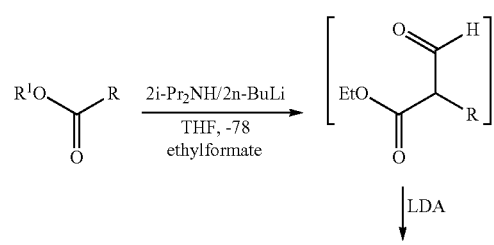

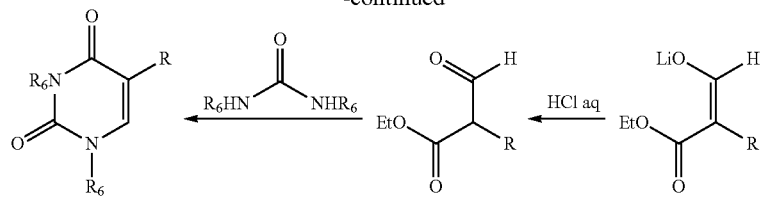

Formula C
R = Z—(CH$_2$)$_w$—X—(CH$_2$)$_y$-

The variables in Formula C in Scheme 6 are as follows:
R can be H, alkyl, aryl, heteroaryl, alicyclic, heterocyclic or —(CH$_2$)$_m$CO$_2$R$_7$, wherein m is an integer greater than 1;
y and w are integers, the sum of which is greater than or equal to 8;
X can be —CH$_2$—, —CR$_8$R$_9$—, —O—, —S— or —NR$_2$—;
Z can be H, —CH$_3$ or —C(=O)Q;
Q can be —OH, —OR$_3$, —NR$_4$R$_5$ or —NHOH;
R$_1$-R$_9$ can each be independently H, alkyl, aryl, heteroaryl, alicyclic or heterocycli The reaction between the PMD ring and a variety of long-chain aldehydes was employed to prepare several long-chain PMD derivatives.

Synthesis of 5-substituted-2-thioxo-2,3-dihydropyrimidin-4(1H)-one Derivatives

General Procedure D

The general procedure for the reaction for obtaining long-chain derivatives of 5-substituted-2-thioxo-2,3-dihydropyrimidin-4(1H)-one derivatives (TPMD), encompassed by Formula II, is illustrated in Scheme 6 hereinbelow.

The synthesis of TPMD is similar to that of PMD presented hereinabove except that thiourea or N,N'-disubstituted thiourea is used instead of urea or an N,N'-disubstituted urea to obtain a long-chain TPMD derivative.

The variables in Formula D in Scheme 7 are as follows:
R can be H, alkyl, aryl, heteroaryl, alicyclic, heterocyclic or —(CH$_2$)$_m$CO$_2$R$_7$, wherein m is an integer greater than;
y and w are integers, the sum of which is greater than or equal to 8;
X can be —CH$_2$—, —CR$_8$R$_9$—, —O—, —S— or —NR$_2$—;
Z can be —CH$_3$ or —C(=O)Q;
Q can be —OH, —OR$_3$, —NR$_4$R$_5$ or —NHOH;
R$_1$-R$_9$ can each be independently H, alkyl, aryl, heteroaryl, alicyclic or heterocycli Example 2

Anti-Biofilm Formation Activity

Anti-Biofilm Formation Activity Assays in Bacteria

Biofilm-formation inhibition (quorum sensing inhibition or QSI):

A series of *V. harveyi* strains (wild-type and mutants), marine bacteria which are used as a widely accepted model for testing quorum sensing, was used in the experiments below. In order to assure that the anti-biofilm forming agents (ABF) according to embodiments of the present invention are quorum sensing inhibitors (QSI) and substantially do not exert bactericidal activity per se, the MICs of exemplary anti-biofilm forming agents were determined as presented hereinbelow.

Scheme 7

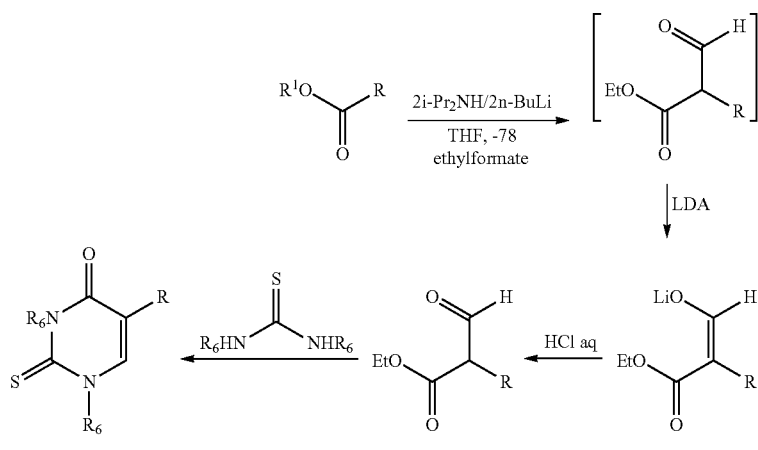

Formula D
R = Z—(CH$_2$)$_w$—X—(CH$_2$)$_y$-

MIC was determined according to the CLSI, formerly NCCLS (National Committee for Clinical Laboratory Standards) recommendation for broth dilution antibacterial susceptibility test.

All the tested *V. harveyi* strains (adjusted to 0.5 MacFarlane standard suspension) were grown at 30° C., in the presence of the tested agent at concentrations ranging from 2 μM to 10 mM, in 96-well transparent micro-titration plates (NUNC, Denmark).

After 18 hours of incubation, bacterial growth was determined according to the density measured by absorbance at 595 nm (GENios reader TECAN-Austria).

Each experiment was conducted in triplicate samples and repeated three times. Based on MIC results, the exemplary anti-biofilm forming agent with the highest MIC values (lowest antibacterial activity) was selected for the anti-quorum sensing activity screening assay.

Table 1 presents the results of the antibacterial activity (MIC values) of TZD10, an exemplary ABF agent according to embodiments of the resent invention, on a series of mutant strains of *V. harveyi*, determined at concentrations of 0.2 mM, 0.02 mM and 0.002 mM.

TABLE 1

| *V. harveyi* strains | Relevant phenotype | MIC (mM) |
|---|---|---|
| BB170 | Sensor 1$^-$, sensor 2$^+$ AI-1$^+$, AI-2$^+$ | <10 |
| BB886 | Sensor 1$^+$, sensor 2$^-$ AI-1$^+$, AI-2$^+$ | <10 |
| BB721 | Sensor 1$^-$, sensor 2$^-$ AI-1$^+$, AI-2$^+$ LuxO null | <10 |
| JAF375 | Sensor 1$^-$, sensor 2$^-$ AI-1$^+$, AI-2$^+$ | <10 |
| BB120 | Wild-type | <10 |

As can be seen in Table 1, the bactericidal activity assays of TZD10 on a series of *V. harveyi* mutants lacking the quorum sensing sensors sensor-1 and sensor-2 and/or lacking the genes for expressing AI-1 (N-acylhomoserine lactones) and AI-2 (furanosyl borate diester), revealed the lack of antibacterial activity per se of TZD10 in these mutants and wild-type bacteria.

Quorum sensing inhibition of *V. harveyi* by ABF agents:

Mutant strains of *V. harveyi*, which are impaired at different locations of the quorum sensing (QS) cascade (see, Table 1 hereinabove) were used for the QSI assays. Bacteria were grown to cell density of 1.5-2.5×10$^9$ CFU/ml (15-16 hours) in AB medium at 30° C. with constant shaking. The fresh cultures were then diluted 5000-fold in fresh AB medium containing TZD10, an exemplary ABF agent according to embodiments of the present invention, at concentrations of 0.02, 0.2, 20 and 200 μM. Each tested concentration was exposed to spent medium of *V. harveyi* MM30 (AI-1$^+$, AI-2$^-$) containing AI-1, or to spent medium of *V. harveyi* BB152 (AI-1$^-$, AI-2$^+$) containing AI-2, or to a control spent medium of *V. harveyi* MM77 (AI-1$^-$, AI-2$^-$) (AI-0) to examine the effect on bioluminescence by the tested concentration with no added auto inducers (AIs). Each sample was also tested without the spent medium as control in order to examine potential self-induction. The negative control contained bacteria in fresh AB medium and the positive control contained bacteria, fresh AB medium and 10% (v/v) spent medium with the appropriate autoinducer (*V. harveyi* BB152 or MM30 spent medium).

The assay was conducted in white 96-well microtitraton plates with a clear bottom (NUNC, Denmark). Luminescence was measured continuously by a GENios reader (TECAN, Austria) every 30 minutes and the bacterial density was determined (O.D. 595 nm).

Each sample was tested in three separate biological experiments, each conducted in triplicate samples. The effect of the ABF agent was determined relatively to the endogenous level of luminescence expressed by *V. harveyi* BB120, BB721, BB170, BB886 and JAF375 relative to the OD, by calculating the area under the curve (AUC) between 3.5-7 hours, applying the trapezoid rule for AUC calculation.

The effect of the various concentrations of TZD10 (namely 0.02 μM, 0.2 μM, 2 μM and 20 μM) on the various *V. harveyi* strains in planktonic environment supplement is illustrated in FIGS. 2A-C.

FIGS. 2A-C present the effect of TZD10, an exemplary ABF agent according to embodiments of the present invention, on quorum sensing in *V. harveyi* strains BB120 (wild type), BB170 (sensor 1$^-$), BB886 (sensor 2$^-$), BB721 (LuxO null) and JAF375 (sensor 1$^-$ and 2$^-$) in planktonic conditions, by following omitted luminescence as an indicator of quorum sensing, with the addition of 10% v/v spent medium of AI-1 (FIG. 2A), AI2 (FIG. 2B) and MO (FIG. 2C), showing a classic dose-response curve and thereby demonstrating the effectiveness of the ABF agent in *V. harveyi* regardless of the presence or absence of AI or quorum sensing genes.

Effect of ABF Agents on Qs in *V. harveyi* in Planktonic and Biofilm Forms:

The working protocol for the biofilm disruption assays were conducted as follows. The tested *V. harveyi* strains (BB120, BB721, BB170, BB886) were grown to cell density of 1.5-2.5×10$^9$ CFU/ml (15-16 hrs) in AB medium at 30° C. with constant shaking and the suspension was diluted (1:5, 000) in fresh AB medium. Aliquot of the suspension (200 μl) was added to each well in a white 96-well plate (NUNC) and incubated for 18 hours at 30° C. without shaking. The formed biofilm was carefully washed twice with saline. Fresh AB medium containing the exemplary ABF agent at the various tested concentrations, and either 10% (v/v) spent medium of *V. harveyi* MM30 (containing AI-1) or 10% (v/v) spent medium of *V. harveyi* BB152 (containing AI-2) were added, for further 18 hours of incubation as described above. Each sample was also tested without the spent medium as control to examine self induction. Positive and negative controls were included as described above. Each sample was tested in three separate biological experiments in triplicate samples. Luminescence was calculated as the AUC using the trapezoid rule.

FIGS. 3A-C present the effect of TZD10, an exemplary ABF agent according to embodiments of the present invention, on *V. harveyi* mutants (BB120 (wild type), BB170 (sensor 1$^-$), BB886 (sensor 2$^-$), BB721 (LuxO null), JAF375 (sensor 1$^-$ and 2$^-$) in mature biofilm conditions, by following omitted luminescence as an indicator of quorum sensing, with the addition of 10% (v/v) spent medium of AI-1 (FIG. 3A), AI-2 (FIG. 3B) and AI-0 (FIG. 3C).

As can be seen in FIGS. 3A-C, a positive dose response was observed between QS inhibition and TZD10 concentrations measured in all tested strains. Since it is expected that the effectiveness of an ABF agent will be reduced in imbedded bacteria (in a biofilm form), a higher range of TZD10 concentrations was used on the immobilized bacteria relative to the effective concentration in the planktonic form.

As can be seen in FIG. 3A, at a TZD10 concentration of 2 μM, QS activity in the biofilms of the strain lacking sensor 2 (BB886) and the wild type (BB120) showed minimal reduction (10% and 18% respectively), while at 0.200 μM TZD10 QSI activity was reduced by 62% in the wild-type and 39% in BB886 strains.

As can be seen in FIG. 3B, *V. harveyi* biofilms that were exposed to AI-2 were less affected by TZD10 than in the presence of AI-1, and at 2 µM TZD10 QSI activity was reduced by 25% in LuxO null strain (BB721), while a minor increase in QSI was observed in the immobilized wild-type strain (BB120) and the mutant lacking sensor 1 (BB170). At the maximal tested concentration, QSI was reduced by 35% in wild-type, 44% in BB170 and 72% in BB721 strain.

As can be seen in FIG. 3C, BB721 strain was most sensitive to the effect of TZD10 on mature *V. harveyi* biofilm with no addition of AI-1 nor AI-2. The QSI activity of the exemplary ABF agent was reduced by 38%, 63% and 79% at 2 µM, 20 µM and 200 µM respectively. In the BB886 strain, QSI activity was reduced by 30% at 2 µM and by 40% at 200 µM. TZD10 showed no effect at 2 µM on the BB170 strain, immobilized in biofilm, but a 62% reduction at the highest tested concentration of 0.200 µM of TZD10.

Biofilm disruption in *V. harveyi* by ABF agents:

The biofilm eradication concentration (BEC) for exemplary ABF agents according to embodiments of the present invention was measured as the effect of the tested agent on mature and fully formed biofilm.

The effect of TZD10, an exemplary ABF agent according to embodiments of the present invention, on the depth and the density of the biofilm was determined using fluorescent stains analyzed by computer image analysis using confocal scanning laser microscopy (CLSM).

Briefly, biofilms were allowed to form in sterile micrtiture dishes as described hereinabove. After washing the formed biofilm, fresh AB medium and an appropriate medium containing TZD10 were added and incubated for additional 18 hours. Bacteria in biofilm were stained with fluorescent dyes to detect the biofilm.

The stained biofilms were examined with a Zeiss LSM 410 confocal laser scanning system attached to a Zeiss Axiovert inverted microscope fitted with a 40×/1.3 Plan-Neofluar lens. In each experiment, exciting laser intensity, background level, contrast and electronic zoom size were maintained at the same level. At least 3 random fields for each experiment were chosen and scored from each sample. Biofilm structure was analyzed as a series of horizontal opto-digital sections. Z-series of optical sections were acquired at spacing steps of 6.75 µm interval from the biofilm base through the vertical axis of the specimen by a computer-controlled motor drive. Image processing of the stained biofilms was done by Image-Pro plus program (Media Cybernetics. Silver Spring, Md., USA) to calculate the relative amount of bacteria (green stained). Each sample was tested in triplicates samples in three separate biological experiments.

FIGS. 4A-D present photographs of the luminescent *V. harveyi* cells immobilized in the form of biofilms, showing the biofilm disruption effect of TZD10, an exemplary ABF agent according to embodiments of the present invention, on matured biofilms of *V. harveyi* wild-type strain (BB120) at different concentrations of 0 µM control (FIG. 4A), 2 µM (FIG. 4B), 20 µM (FIG. 4C) and 200 µM (FIG. 4D), wherein the biofilms are visualized by green emission, varying in intensities as a function of the amount of labeled bacteria, corresponding to the depth of the biofilm staring from the surface interface to the air/water interface, and wherein each of the individual frames represent the depth of the biofilm depth of the biofilm in microns, going row-wise from 0 micron at the top-left frame to 75 microns at the bottom-right frame.

As can be seem in FIGS. 4A-D, TZD10 at concentarions lower than its MIC exhibits a dose response effect of biofilm disruption, demonstrating its effectiveness in eradicating bacterial biofilms.

Anti-Biofilm Formation Activity Assays in Fungi

*Candida albicans* (ATCC 90028) was used to study the anti-biofilm formation activity of exemplary ABF agents according to embodiments of the present invention.

The *C. albicans* strain was propagated in yeast peptone dextrose (YPD) medium (1% wt/vol yeast extract, 2% wt/vol peptone, 2% wt/vol dextrose). Batches of medium (30 ml in 125 ml Erlenmeyer flask) were inoculated with material from Sabouraud dextrose agar (SDA) plates containing freshly grown *C. albicans* and incubated overnight in an orbital shaker (200 rpm) at 30° C. under aerobic conditions. *C. albicans* grew in the budding-yeast phase under these conditions. Cells were harvested and washed twice in sterile phosphate-buffered saline (PBS) (Oxoid Ltd, Basingstoke, Hampshire, UK). Thereafter the cells were resuspended in RPMI 1640 supplemented with L-glutamine and buffered with morpholinepropanesulfonic acid (MOPS) (Sigma Chemical Co., St. Louis, Mo.) and adjusted to the desired density after counting with a hematocytometer.

Formation of *C. albicans* Biofilm:

Biofilms of *C. albicans* were formed in the wells on commercially available presterilized, polystyrene, flat-bottomed, 96-well microtiter plates (Nunc—Nunclon™ Surface, Roskilde, Denmark). Biofilms were formed by pipetting 100 µl of the standardized cell suspensions (5×10⁶ cells/ml) into selected wells of the microtiter plate and incubating the plate for 72 hours at 37° C. After 24 hours and 48 hours of the biofilm formation, the medium was replaced by fresh RPMI 1640 medium.

Effect of farnesol and anti-biofilm formation agent on biofilm formation:

As presented hereinabove, fungi communicate between themselves also with signal molecules, and the production of farnesol by *C. albicans* at high cell densities was the first QS system to be discovered in eukaryotes. Farnesol has been identified as a QS agent that blocks the morphological transition from yeast to the filament form and affects biofilm formation in *C. albicans*.

Farnesol

Farnesol (Sigma-Aldrich, In, St. Louis, Mo.) was diluted to obtain a 30 mM working stock solution in 100% (vol/vol) methanol. The exemplary ABF agents according to embodiments of the present invention, (Z)-5-decylidenethiazolidine-2,4-dione (TZD10) and (Z)-5-undecylidenethiazolidine-2,4-dione (TZD11), were diluted in 99.8% DMSO to obtain a 10 mg/ml working stock solution.

Working concentrations of farnesol (300 µM; 66 µg/ml) and the exemplary ABF agents TZD10 and TZD11 (200 µg/ml) were prepared in RPMI 1640 by using the stock solutions. Standardized cell suspensions (100 µl portions at final concentration of 2.5×10⁶ cells/ml) were seeded into selected wells of the 96-well microtiter plate. The tested sample (farnesol at a final concentration of 150 µM (33 µg/ml), and the ABF agents TZD10 and TZD11 at the final concentrations of 25, 50, 100 µg/ml), were added (100 µl portions to each well) to a standardized cell suspension. In addition, the effect of antifungal agent fluconazole at the concentrations of 31.25, 62.5 or 125 µg/ml on biofilm formation was also examined. The plate was incubated for 72 hours at 37° C. as described above.

In another experiment, the tested compounds (farnesol and the present ABF agents) were removed from the wells after 48 hours of incubation and fluconazole was added at a concentration of 31.25 µg/ml. The plate was incubated for additional 24 hours at 37° C.

The effect of the compounds on biofilm formation was measured by using a metabolic reduction assay (XTT kit). Briefly, 100 µl of the XTT reaction solution (Biological Industries, Israel Beit Haemek Ltd.) was added to each well, and microtiter plate was then incubated in the dark for 2 hours at 37° C. The colorimetric change (a reflection of the metabolic activity of the biofilm) was measured with a microtiter plate reader at 492 nm. The anti-biofilm formation activity effect of the tested agents was expressed as the percentage of the optical density (OD) of the treated wells compared to that of control (untreated) wells for the XTT assays. Light microscopic examination of biofilms formed in microtiter plates was performed in parallel by using an inverted microscope.

FIG. 5 presents a comparative bar-graph of the results of the QSI experiments in the fungus *C. albicans* as assessed by colorimetric assay and microscopy, which demonstrated that incubation of *C. albicans* yeast cells (in planktonic form) with farnesol, the exemplary ABF agents TZD10 and TZD11, according to embodiments of the present invention, and antifungal agent fluconazole, showing that the present ABF agents inhibited germination and substantially prevented biofilm formation.

As can be seen in FIG. 5, farnesol at a concentration of 33 µg/ml caused 43% reduction in the metabolic activity of the yeast cells as measured by XTT assay, while lower concentration of the ABF agents according to the present embodiments (25 µg/ml) exhibited similar activity on biofilm formation (47% inhibition). When *C. albicans* were exposed to the higher concentration of the ABF agents (100 µg/ml), greater reduction in the metabolic activity of the yeasts was detected (up to 72%). As can also be seen in FIG. 5, the antifungal agent fluconazole was also active at all concentrations tested (31-125 µg/ml) against biofilm formation and caused up to 77% reduction in the metabolic activity.

FIG. 6 presents a comparative bar-graph of the results of the QSI experiments in the fungus *C. albicans* as presented in FIG. 5, whereas in this experiments the ABF agents were removed after 48 hours and fluconazole 31.25 µg/ml was introduced for another 24 hours.

As can be seen in FIG. 6, when exemplary ABF agents were combined with fluconazole (31.25 µg/ml), higher reduction in the biofilm metabolic activity was detected. In contrast, the combination of Farnesol and fluconazole did not show any additive effect when compared to farnesol alone.

Effect of farnesol and anti-biofilm agents on matured biofilm and synergism studies:

*C. albicans* biofilm was formed during 48 hours at 37° C. on the surfaces of microtiter plates by using the protocol described hereinabove, and the tested ABF agents were then added to the preformed biofilm. Following biofilm formation the spent medium and the nonadherent cells were removed by washing the biofilms three times in sterile PBS. The tested compounds, the ABF agent at 25, 50, 100 µg/ml, fluconazole at 31.25, 62.5, 125 µg/ml, in fresh RPMI 1640—farnesol at 150 µM (33 µg/ml), were added to selected wells of the microtiter plates. In addition, the effect of combination of farnesol (33 µg/ml) with fluconazole (31.25 µg/ml) and the ABF agent (25 or 50 µg/ml) with fluconazole (31.25 µg/ml) was examined on preformed biofilms. The plates were then incubated for 24 hours at 37° C. The effect of the compounds on pre-formed biofilms was then estimated by using the XTT reduction assay as described hereinabove.

FIG. 7 presents comparative bar-graph of the synergistic effect of farnesol and one of the exemplary ABF agents TZD10 and TZD11, on mature biofilm of *C. albicans* without the presence of fluconazole.

As can be seen in FIG. 7, the ABF agents exhibited a profound anti-biofilm effect on the fungi while no activity was observed with farnesol and fluconazole on the preformed biofilm. In contrast, the thiazolidinediones were active against the preformed *C. albicans* biofilm, as expressed in the reduction of the biofilm metabolic activity up to 40% compared to the control.

FIG. 8 presents comparative bar-graph of the synergistic effect of farnesol and one of the exemplary ABF agents TZD10 and TZD11, on mature biofilm of *C. albicans* with the presence of fluconazole.

As can be seen in FIG. 8, no additive anti-biofilm effect was observed on the pre-formed biofilm by the addition of fluconazole (31.25 µg/ml) to farnesol (33 µg/ml). Moreover, higher reduction (up to 55%) in the biofilm metabolic activity was observed when fluconazole (31.25 µg/ml) was added to the ABF agents.

Example 3

Cell Harvesting

Vero cells detachment by ABF agents:

The detachment of Vero cells by TZD10, an exemplary ABF agent according to the present invention, was examined following the method presented hereinbelow.

Vero cells (0.1 ml, 1.6×10$^6$ cells/ml) were plated in each well of flat 96-wells polystyrene plate (Nunc), and incubated overnight at 37° C. and 5% CO$_2$. The cells were then incubated with various concentrations of the exemplary tested ABF agent TZD10.

At the indicated time intervals, the cells were washed and re-suspended in fresh medium. XTT (2,3-bis-(2-methoxy-4-nitro-5-sulfophenyl)-2H-tetrazolium-5-carboxanilide) analysis was performed to determine the viability of the attached cells.

FIG. 9 presents a comparative bar-graph showing the results of the Vero cells detachment assay using TZD10, an exemplary ABF agent according to the present embodiments, demonstrating the effectiveness of TZD10 to detach living cells from the cell-aggregate.

FIG. 10 presents a bar-graph showing the results of the Vero cells detachment assay after overnight incubation with 50 µg/ml of TZD10, an exemplary ABF agent according to the present embodiments, demonstrating that most of the cells are still viable.

As can be seen in FIGS. 9 and 10, most of the cells were detached after 30 minutes of treatment with 100 µg/ml of TZD10, or after 5 minutes of treatment with 200 µg/ml of TZD10. TZD10 was not completely soluble at a concentration of 100 µg/ml and above, and at a concentration of 200 µg/ml there was a significant amount of TZD10 crystals at the bottom of the well (at a concentration of 100 µg/ml there were crystals also but in much less extend), indicating that the ABF agent is active at a lower concentration than reported herein.

The effect of TZD10 on the viability of Vero cells was detected by incubating the cells for 40 minutes with TZD10, and further incubation for 120 minutes with the XTT reagents in the same medium without washings, so that the total incubation time with TZD10 was 160 minutes. The cells were treated with TZD10 for 40 minutes without the XTT reagents that were then added for further 120 minutes incubation.

FIG. 11 presents the results of the Vero cell viability assay, wherein the cell viability was measured after 160 minutes incubation with TZD10.

As can be seen in FIG. 11, the ABF agent is not toxic to the cells at a concentration of up to 100 μg/ml, and partially cytotoxic at higher concentrations of 125 μg/ml and above.

Vero cells detachment from T-flasks:

Vero cells were grown on for 6 days in T-flask with DMEM+10% FCS+Hepes+Glutamine+Pen-strep (Beit HaEmek). The cells were then washed with PBS and incubated for 40 minutes with 100 μg/ml TZD10+1.34 mM (about 0.5 mg/ml) EDTA in PBS without calcium and magnesium (Beit HaEmek).

Microscopic analysis revealed that after this treatment the cells could be released from the flask by pipettetion. The detached cells were not separated from each other and they were plated in a T-flask with the same growth medium lacking the drugs and were further incubated. After 1 day the cells were attached to the T-flask and started to divide, forming clumps of biomass rather than a monolayer. After another 4 days, the divided cells produced new monolayer around these clumps.

SAR for ABF Agents in Vero Cells Detachment Assay:

FIG. 12 presents a bar-graph showing the results obtained for a series of ABF agents, according to some embodiments of the present invention, which were tested as suitable for Vero cell harvesting.

The mode of action of TZD10 in detachment of Vero cells:

Without being bound to any particular theory, it is hypothesized that the detachment of the cells by the treatment with TZD10 is due to the release of cell proteases which digest proteins that are responsible to the connection to the polystyrene plate. In order to study this hypothesis Vero cells were incubated for 15 minutes with medium including 100 μg/ml TZD10, and then the medium was tested for protease activity using SIGMA-Protease fluorescent detection kit.

No evidence for the presence of proteases was found (data not shown).

TZD10 effect on MDCK cells:

Madine-Derby canine kidney cells (MDCK) are a non-cancerous, polarized epithelial cell line, used in the research of cell polarity mechanisms, and in the research of pathogen interactions with epithelial tissues. These cells produce monolayers in which cells are polarized and tightly connected to each other. The cells were treated with TZD10 for 40 minutes without the XTT reagents that were then added for further 120 minutes incubation.

MDCK cells were also detached from the polystyrene dish using TZD10, but did not exhibit free-floating cell forms.

The influence of TZD10 on the attachment of MDCK cells was investigated using an identical method used for the Vero cells (the 96 well polystyrene plate method) as presented hereinabove.

FIGS. 13A-B present bar-graphs, showing the results of the assay for detachment of MDCK cells by TZD10, an exemplary ABF agent according to some embodiments of the present invention (FIG. 13A), and the MDCK cells viability assay after incubation with TZD10 (FIG. 13B).

As can be seen in FIGS. 13A-B, the detachment of the MDCK cells was observed sooner than it has been observed with Vero cells, however, TZD10 was found to be more toxic to MDCK cells than to Vero cells.

Example 4

Biofilm Prevention and Suppression on Surfaces

As discussed hereinabove the anti-biofilm formation (ABF) agents presented herein, such as the exemplary TZD10 and other TZD and PYD compounds, can be attached to various polymers, so as to form conjugates that are applied onto surfaces which are typically in contact with water. These compounds interact with periplasmatic receptors to interfere with QS and thus prevent the formation of biofilms or greatly retard their growth.

Immobilization of ABF agents to surfaces via polymers:

For a non-limiting example, a relatively simple poly-methacrylate-TZD10 monomer that can be readily polymerized and immobilize on polymeric surfaces, is prepared according to the general procedure illustrated in Scheme 7 below, showing the synthesis of methacrylate TZD10 monomer and polymer.

These general procedures presented herein can be applied to any of the ABF agents according to embodiments of the present invention, with some adaptations and modifications according to each particular ABF agent.

Scheme 7

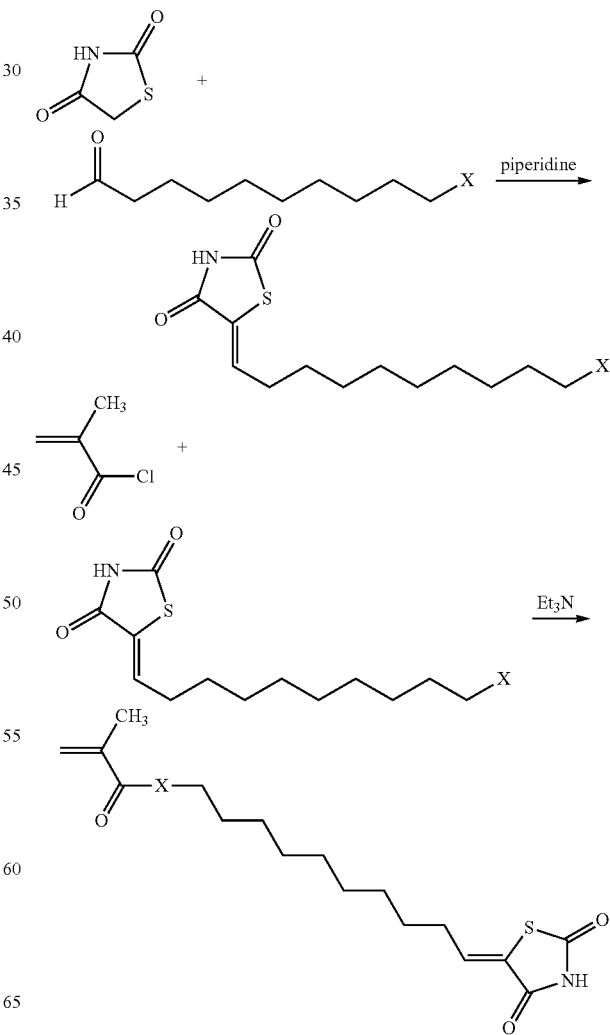

-continued

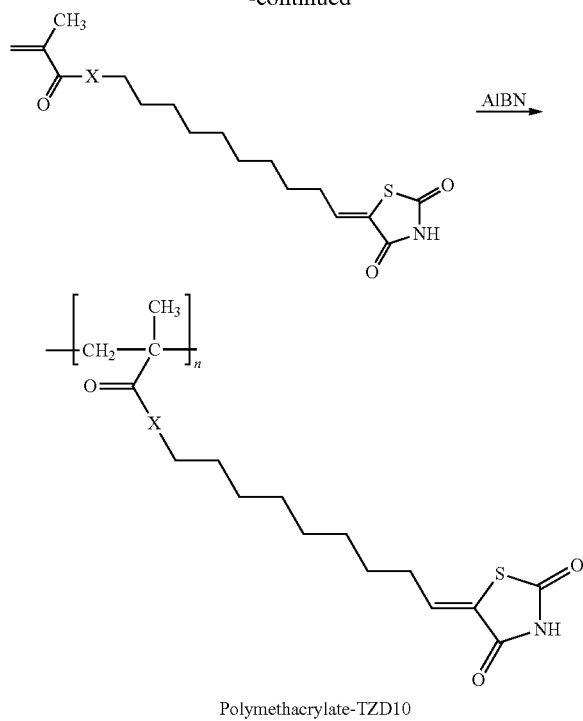

Polymethacrylate-TZD10
X = OH, NH₂

For immobilization on metal surfaces, a PEG polymer is prepared and anchored by, for example, a 1,2-dihydroxyphenyl unit or another group for attaching to metal surfaces, as illustrated in Scheme 8, showing the schematics of a quorum sensing inhibiting (QSI) PEG having a TZD10 group attached thereto.

Scheme 8

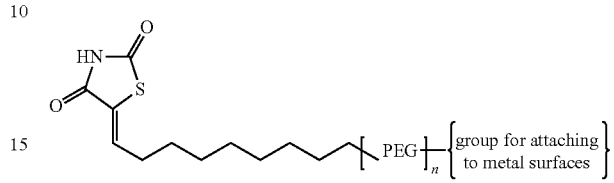

General procedures for preparing such PEG derivative and the conjugate are depicted in Scheme 9, showing the synthesis of methacrylate monomers of TZD10-X-HS-PEG-MA and DOPA-MA, and in Scheme 10 showing the structure of PEG-TZD10-MA and DOPA-MA copolymer.

In Scheme 9 a hemisuccinate-PEG-OH is reacted with the exemplary QSI TZD10-X (X=OH, NH₂) in the presence of dicyclohexylcarbodiimide (DCC) and 4-N,N-dimethylaminepyridine (DMAP) as a catalyst to afford TZD10X-HS-PEG-OH. The latter in turn is condensed with methacroyl-chloride under basic conditions to give the TZD10X-HS-PEG-MA.

Scheme 9

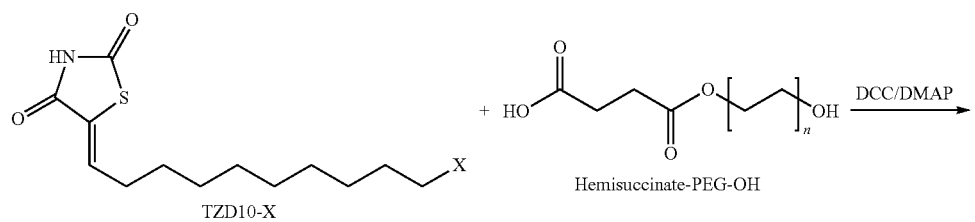

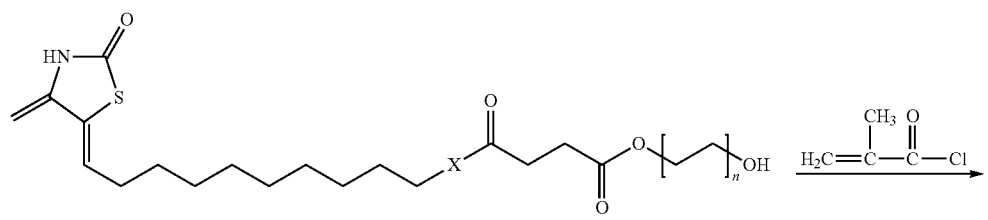

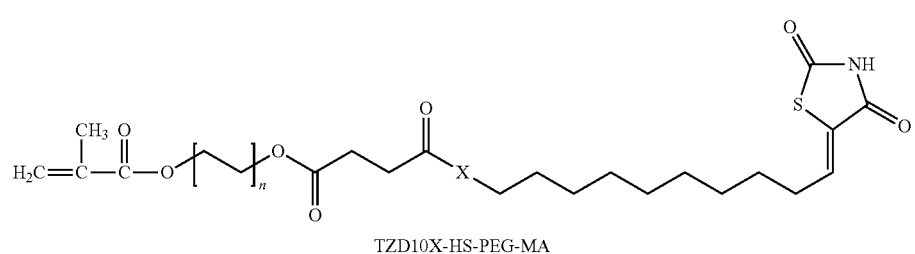

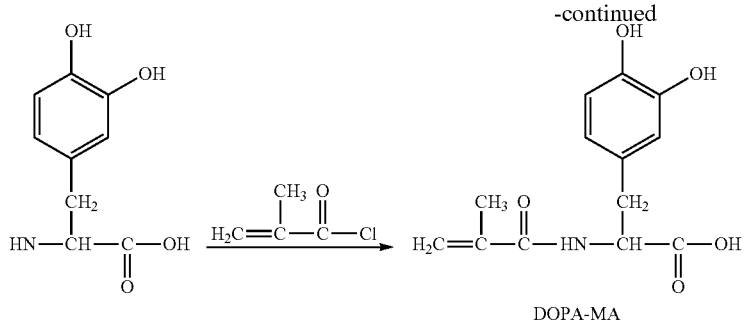

DOPA-MA

X = OH, NH₂

DOPA-MA is prepared from DOPA and methacroylchloride using procedures known in the art, such as the Messersmith reaction. The two methacrylate monomers are photopolymerized as illustrated in Scheme 10 using various initiators to determine optimal conditions such as N-(2,3-dimercaptopropyl)-phthalamidic acid (DMPA), camphorquinone (CA)/amine, or fluorescein sodium salt/ascorbic acid.

Scheme 10

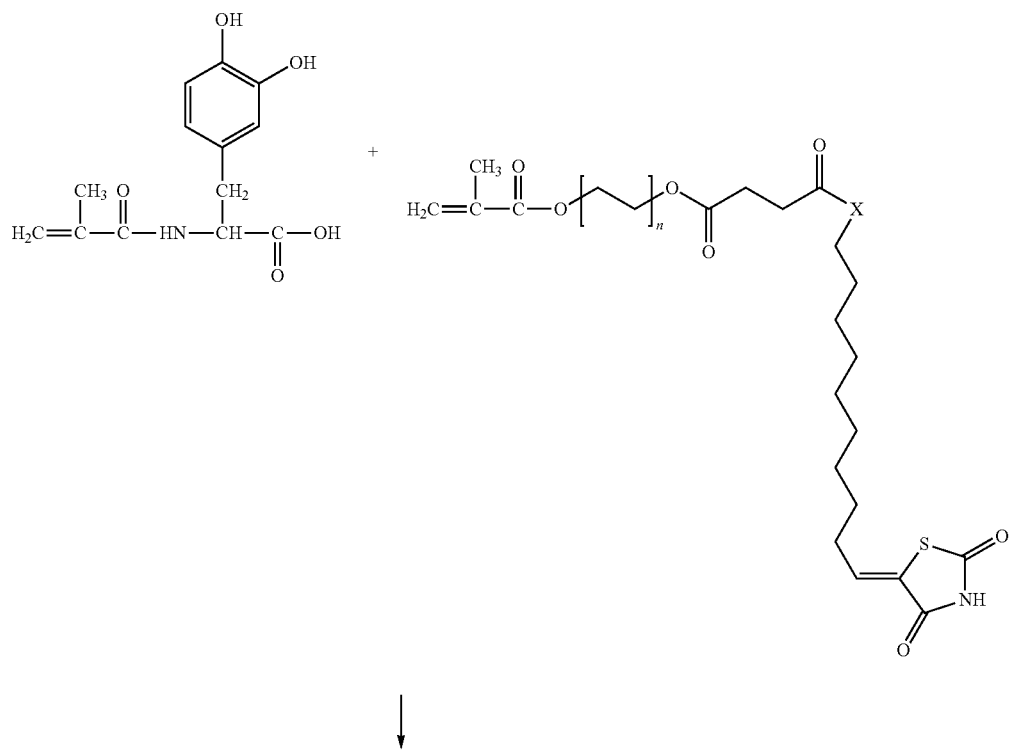

-continued

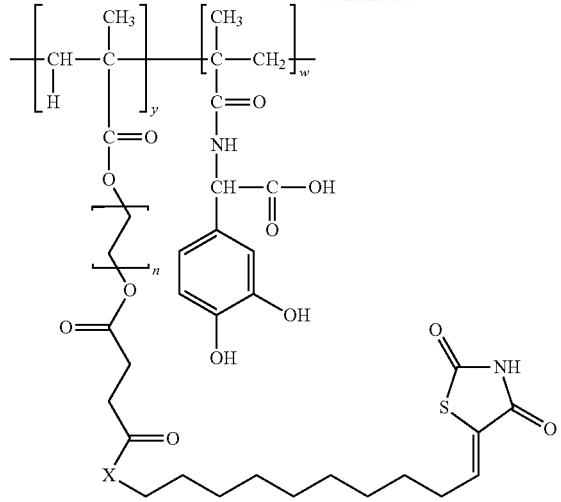

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound having the general formula:

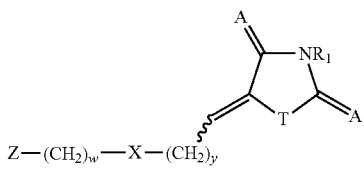

Formula I or a salt thereof,
wherein:
y and w are each independently an integer, such that y+w ranges from 7 to 20;
A is O;
T is selected from the group consisting of —S—, and —CH$_2$—;
R$_1$ is selected from the group consisting of H and —(CH$_2$)$_m$CO$_2$R$_7$;
m is an integer ranging from 1 to 6;
X is selected from the group consisting of —CH$_2$—, —CR$_8$R$_9$—, —O—, —S— and —NR$_2$— or absent;
Z is selected from the group consisting of H, —CH$_3$, —C(=O)Q, a linking moiety selected from the group consisting of amide and ester, a reactive group selected from the group consisting of aldehyde, alkoxy, amine, azide, carbonyl, carboxyl, cyanate, cyano, halo, hydroxy, nitro, sulfonate, thiocyanate. thiohydroxy, tosylate and triflate, a polymer moiety selected from the group consisting of a polyacrylate, a polymethaciylate, a polyethylene glycol (PEG), an oligo/polysaccharide, a peptide, a protein, a nucleic acid, a polyurethane, an epoxy resin, a fluoropolymer, a polyimide, a polyamide, a polyacrylamides and a polyhydroxyethyl methacrylate, and a polymerizable moiety selected from the group consisting of an acrylate, a methacrylate, 2-hydroxyethyl (ethylene glycol), a saccharide, an amino acid residue, a nucleic acid residue, a urethane, an epoxide, fluoroalkene, an amide, imide, an acrylamide, hydroxyethylmethacrylate and N-vinyl-2-pyrrolidinone;
Q is selected from the group consisting of —OH, —OR$_3$, —NR$_4$R$_5$ and —NHOH; and
R$_2$, R$_3$, R$_4$, R$_5$, R$_6$, R$_7$, R$_8$, R$_9$ and R$_{10}$ are each independently selected from the group consisting of H, alkyl, aryl, heteroaryl, alicyclic and heterocyclic.

2. The compound of claim 1, having the general formula:

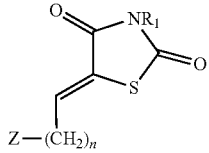

Formula A1 or a salt thereof,
wherein:
n is an integer ranging from 7 to 20; and
R$_3$, R$_4$, R$_5$ and R$_7$ are each independently selected from the group consisting of H, alkyl and aryl.

3. The compound of claim 2, wherein R$_1$ is H.

4. The compound of claim 2, being selected from the group consisting of:

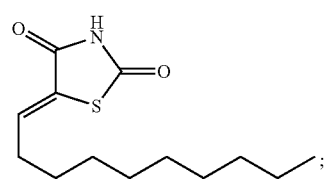

(TZD10)

(Z)-5-decylidenethiazolidine-2,4-dione

-continued

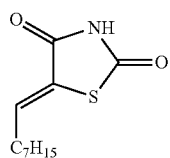
(Z)-5-octylidenethiazolidine-2,4-dione; (TZD8)

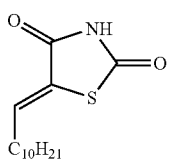
(Z)-5-undecylidenethiazolidine-2,4-dione; (TZD11)

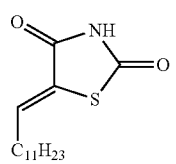
(Z)-5-dodecylidenethiazolidine-2,4-dione; (TZD12)

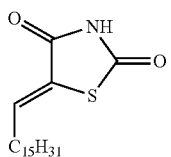
(Z)-5-hexadecylidenethiazolidine-2,4-dione; and (TZD16)

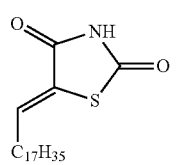
(Z)-5-octadecylidenethiazolidine-2,4-dione. (TZD18)

5. The compound of claim 2, wherein $R_1$ is said $-(CH_2)_m CO_2R_7$.

6. The compound of claim 5, being selected from the group consisting of:

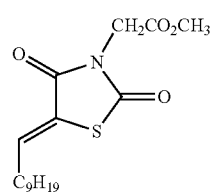
(Z)-methyl 2-(5-decylidene-2,4-dioxothiazolidin-3-yl)acetate; (TZD10MA)

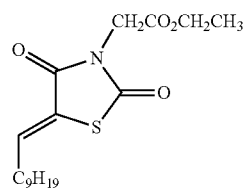
(Z)-ethyl 2-(5-decylidene-2,4-dioxothiazolidin-3-yl)acetate; (TZD10EA)

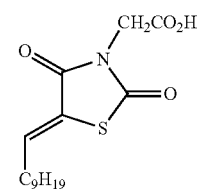
(Z)-2-(5-decylidene-2,4-dioxothiazolidin-3-yl)acetic acid; and (TZD10AA)

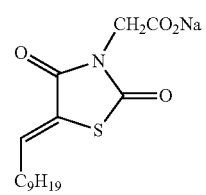
sodium (Z)-2-(5-decylidene-2,4-dioxothiazolidin-3-yl)acetate. (TZD10AANa)

7. The compound of claim 1, wherein T is —S—.
8. The compound of claim 1, wherein $R_1$ is H.
9. The compound of claim 1, wherein X is absent.
10. The compound of claim 7, wherein X is O.
11. The compound of claim 1, wherein T is $CH_2$.
12. The compound of claim 11, wherein $R_1$ is H.
13. The compound of claim 11, wherein X is absent.
14. The compound of claim 13, being selected from the group consisting of:

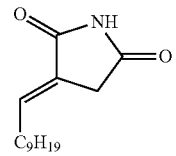
(E)-3-decylidenepyrrolidine-2,5-dione; and (PYD10)

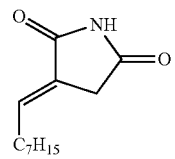
(E)-3-octylidenepyrrolidine-2,5-dione. (PYD8)

15. A composition comprising, as an active ingredient, the compound of claim 1 and a carrier.

16. The composition of claim 15, being packaged in a packaging material and identified in print, in or on said packaging material, for use in a method of preventing or reducing a formation of a biofilm or disrupting a biofilm.

17. The composition of claim 15, further comprising at least one additional active agent.

18. The composition of claim 17, wherein said additional active agent is an antimicrobial agent.

19. A compound having the general formula:

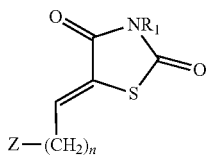

Formula A1 or a salt thereof,
wherein:
n is an integer ranging from 7 to 20;
$R_1$ is selected from the group consisting of H and —$(CH_2)_m CO_2 R_7$;
m is an integer ranging from 1 to 6;
Z is selected from the group consisting of H, —$CH_3$, —C(=O)Q, a linking moiety selected from the group consisting of amide and ester, a reactive group selected from the group consisting of aldehyde, alkoxy, amine, azide, carbonyl, carboxyl, cyanate, cyano, halo, hydroxy, nitro, sulfonate, thiocyanate, thiohydroxy, tosylate and triflate, a polymer moiety selected from the group consisting of a polyacrylate, a polymethacrylate, a polyethylene glycol (PEG), an oligo/polysaccharide, a peptide, a protein, a nucleic acid, a polyurethane, an epoxy resin, a fluoropolymer, a polyimide, a polyamide, a polyacrylamides and a polyhydroxyethyl methacrylate, and a polymerizable moiety selected from the group consisting of an acrylate, a methacrylate, 2-hydroxyethyl (ethylene glycol), a saccharide, an amino acid residue, a nucleic acid residue, a urethane, an epoxide, a fluoroalkene, an amide, an imide, an acrylamide, hydroxyethylmethacrylate and N-vinyl-2-pyrrolidinone;
Q is selected from the group consisting of —OH, —$OR_3$, —$NR_4R_5$ and —NHOH; and
$R_3$, $R_4$, $R_5$ and $R_7$ are each independently selected from the group consisting of H, alkyl and aryl.

20. A compound selected from the group consisting of:

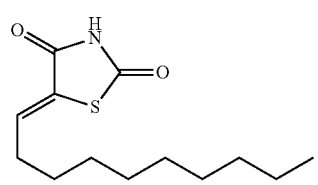

(Z)-5-decylidenethiazolidine-2,4-dione;

(Z)-5-octylidenethiazolidine-2,4-dione;

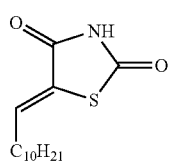

(Z)-5-undecylidenethiazolidine-2,4-dione;

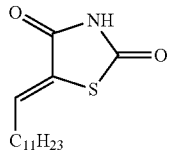

(Z)-5-dodecylidenethiazolidine-2,4-dione;

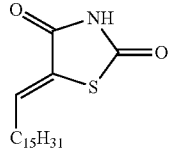

(Z)-5-hexadecylidenethiazolidine-2,4-dione;

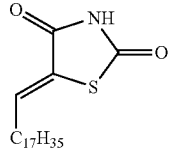

(Z)-5-octadecylidenethiazolidine-2,4-dione;

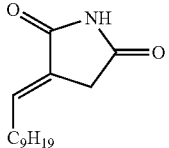

(E)-3-decylidenepyrrolidine-2,5-dione; and

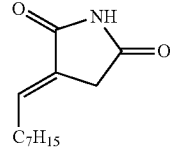

(E)-3-octylidenepyrrolidine-2,5-dione.

21. A compound:

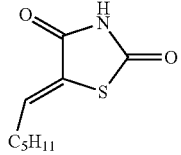

(Z)-5-hexylidenethiazolidine-2,4-dione.

* * * * *